(12) United States Patent
Wawro et al.

(10) Patent No.: US 11,389,063 B2
(45) Date of Patent: Jul. 19, 2022

(54) MODULAR VITAL SIGNS MONITOR

(71) Applicant: C/O Welch Allyn, Inc., Skaneateles Falls, NY (US)

(72) Inventors: Thaddeus J. Wawro, Auburn, NY (US); Timothy R. Fitch, Syracuse, NY (US); Carlos Andres Suarez, Syracuse, NY (US); Scott Andrew Martin, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 302 days.

(21) Appl. No.: 16/150,572

(22) Filed: Oct. 3, 2018

(65) Prior Publication Data

US 2019/0150739 A1  May 23, 2019

Related U.S. Application Data

(60) Provisional application No. 62/588,598, filed on Nov. 20, 2017, provisional application No. 62/592,602,
(Continued)

(51) Int. Cl.
*A61B 5/00* (2006.01)
*A61B 5/259* (2021.01)
(Continued)

(52) U.S. Cl.
CPC ............ *A61B 5/0022* (2013.01); *A61B 5/259* (2021.01); *A61B 5/332* (2021.01); *A61B 5/02416* (2013.01);
(Continued)

(58) Field of Classification Search
CPC . A61B 5/0022; A61B 5/0404; A61B 5/04087; A61B 5/02416; A61B 5/02438;
(Continued)

(56) References Cited

U.S. PATENT DOCUMENTS

| 4,448,199 A | 5/1984 | Schmid |
| 4,583,549 A * | 4/1986 | Manoli ................. A61B 5/411 |
| | | 600/397 |

(Continued)

FOREIGN PATENT DOCUMENTS

| CA | 2959919 A1 | 5/2017 |
| EP | 1708613 B1 | 8/2005 |

(Continued)

OTHER PUBLICATIONS

International Search Report; PCT/US2018/061246; International filing date Nov. 15, 2018; dated Nov. 29, 2017; Applicant Welch Allyn, Inc.; 9-pages.

(Continued)

*Primary Examiner* — Carl H Layno
*Assistant Examiner* — Michael J Lau
(74) *Attorney, Agent, or Firm* — Barnes & Thornburg LLP

(57) ABSTRACT

A vital signs monitor includes a subject wearable first cleat having a first sensor opening and a pair of laterally spaced apart first electrodes. The monitor also includes a subject wearable second cleat having a pair of laterally spaced apart second electrodes. An equipment housing is removably attached to or attachable to the first and second cleats. The housing has a first sensor pocket which registers with the first sensor opening. The monitor also includes a first sensor aligned with the first sensor opening and the first sensor pocket.

17 Claims, 25 Drawing Sheets

Related U.S. Application Data filed on Nov. 30, 2017, provisional application No. 62/618,772, filed on Jan. 18, 2018.

(51) Int. Cl.
*A61B 5/332* (2021.01)
*A61B 5/024* (2006.01)
*A61B 5/1455* (2006.01)

(52) U.S. Cl.
CPC ......... *A61B 5/02438* (2013.01); *A61B 5/1455* (2013.01); *A61B 5/14551* (2013.01); *A61B 5/6829* (2013.01); *A61B 2560/0443* (2013.01)

(58) Field of Classification Search
CPC . A61B 5/1455; A61B 5/14551; A61B 5/6829; A61B 2560/0443
USPC ....................................................... 600/509
See application file for complete search history.

(56) References Cited

U.S. PATENT DOCUMENTS

| | | | |
|---|---|---|---|
| 5,660,177 A * | 8/1997 | Faupel | A61B 5/05 600/382 |
| 6,073,039 A | 6/2000 | Berson | |
| 6,453,186 B1 * | 9/2002 | Lovejoy | A61B 5/282 600/386 |
| 8,214,007 B2 | 7/2012 | Baker et al. | |
| 8,449,469 B2 | 5/2013 | Banet et al. | |
| 9,237,848 B2 | 1/2016 | Russell | |
| 9,439,566 B2 | 9/2016 | Arne et al. | |
| 9,521,970 B2 | 12/2016 | Hope et al. | |
| 9,585,620 B2 * | 3/2017 | Paquet | G16H 40/67 |
| 2004/0019288 A1 * | 1/2004 | Kinast | A61B 5/0402 600/509 |
| 2005/0113703 A1 * | 5/2005 | Farringdon | A61B 5/11 600/509 |
| 2006/0020217 A1 * | 1/2006 | Lin | A61B 5/02444 600/509 |
| 2008/0114220 A1 * | 5/2008 | Banet | A61B 5/021 600/382 |
| 2009/0076340 A1 * | 3/2009 | Libbus | A61B 5/721 600/301 |
| 2009/0171163 A1 * | 7/2009 | Mates | G16H 40/40 600/300 |
| 2010/0152557 A1 * | 6/2010 | Oh | A61B 5/6816 600/309 |
| 2011/0077497 A1 * | 3/2011 | Oster | A61B 5/259 600/300 |
| 2011/0144463 A1 * | 6/2011 | Pesach | A61B 5/6833 600/345 |
| 2011/0213225 A1 * | 9/2011 | Bernstein | A61B 5/0022 600/309 |
| 2011/0288605 A1 * | 11/2011 | Kaib | A61B 5/053 607/5 |
| 2012/0029308 A1 * | 2/2012 | Paquet | A61B 5/01 600/549 |
| 2012/0089037 A1 * | 4/2012 | Bishay | A61B 5/282 600/509 |
| 2012/0157867 A1 * | 6/2012 | Pekonen | A61B 5/0531 600/509 |
| 2012/0245439 A1 * | 9/2012 | Andre | A61B 5/412 600/310 |
| 2013/0131468 A1 * | 5/2013 | Deck | A61B 5/14503 604/503 |
| 2013/0245480 A1 * | 9/2013 | Crockford | A61B 5/6825 600/521 |
| 2013/0274584 A1 * | 10/2013 | Finlay | A61B 5/0432 600/391 |
| 2013/0317379 A1 * | 11/2013 | Brimer | G16H 20/30 600/538 |
| 2013/0325096 A1 * | 12/2013 | Dupelle | A61B 5/259 607/142 |
| 2014/0246924 A1 * | 9/2014 | Proud | H04B 5/02 307/114 |
| 2015/0094558 A1 * | 4/2015 | Russell | G16H 40/67 600/386 |
| 2015/0190066 A1 * | 7/2015 | Boege | A61B 5/742 600/509 |
| 2015/0335284 A1 * | 11/2015 | Nuovo | A61B 5/7445 600/300 |
| 2015/0351690 A1 * | 12/2015 | Toth | A61B 5/14517 600/391 |
| 2015/0374255 A1 * | 12/2015 | Vasapollo | A61B 5/6814 600/383 |
| 2016/0120433 A1 * | 5/2016 | Hughes | A61B 5/0022 600/483 |
| 2016/0242654 A1 * | 8/2016 | Quinlan | G16H 20/40 |
| 2016/0262485 A1 * | 9/2016 | Walker | A61B 5/6807 |
| 2016/0262644 A1 | 9/2016 | Batzer | |
| 2016/0262649 A1 * | 9/2016 | Hayes-Gill | A61B 5/6833 |
| 2016/0270704 A1 * | 9/2016 | DeTurk | A61B 5/4872 |
| 2017/0038792 A1 * | 2/2017 | Moore | G06F 1/1635 |
| 2017/0049338 A1 * | 2/2017 | Pisani | A61B 5/7285 |
| 2017/0095177 A1 * | 4/2017 | Spencer | A61B 5/332 |
| 2017/0172517 A1 * | 6/2017 | Banet | A61B 5/02055 |
| 2017/0188858 A1 * | 7/2017 | Banet | A61B 5/349 |
| 2017/0188918 A1 * | 7/2017 | Banet | A61B 5/4875 |
| 2017/0265769 A1 | 9/2017 | Quinian et al. | |

FOREIGN PATENT DOCUMENTS

| | | | | |
|---|---|---|---|---|
| WO | 2005070289 A1 | 8/2005 | | |
| WO | 2010107913 A2 | 9/2010 | | |
| WO | 2015002940 A2 | 1/2015 | | |
| WO | WO-2015048298 A1 * | 4/2015 | ............ | A61B 5/274 |
| WO | 2016010983 | 1/2016 | | |

OTHER PUBLICATIONS

Written Opinion of the International Searching Authority; dated Mar. 13, 2019; Applicant's file reference 10475-WOI1; International application No. PCT/US2018/061246; International filing date Nov. 15, 2018; dated Nov. 29, 2017; International Patent Classification A61B 5/04(Jan. 2006)i,A61B 5/00(Jan. 2006.)i; Applicant Welch Allyn, Inc.; 14-pages.

European Search Report for European Patent Application No. 18879946.4 dated Jul. 2, 2021 (4 pages).

* cited by examiner

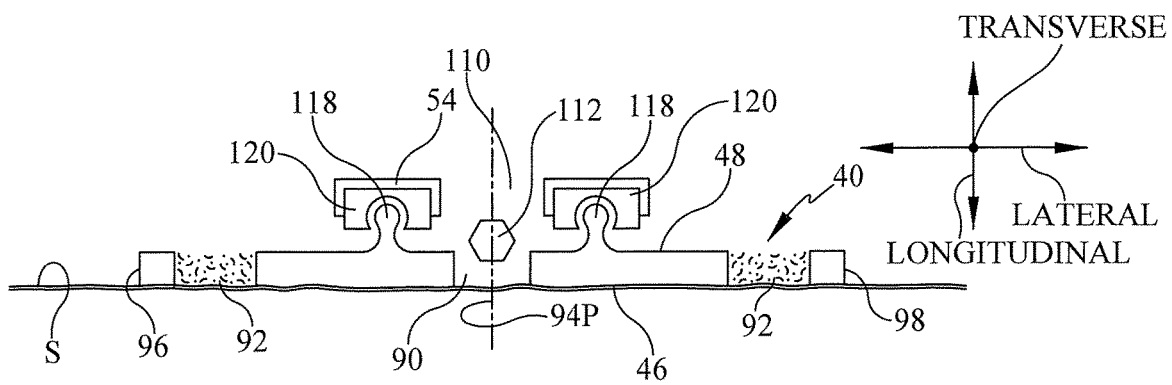
FIG. 4
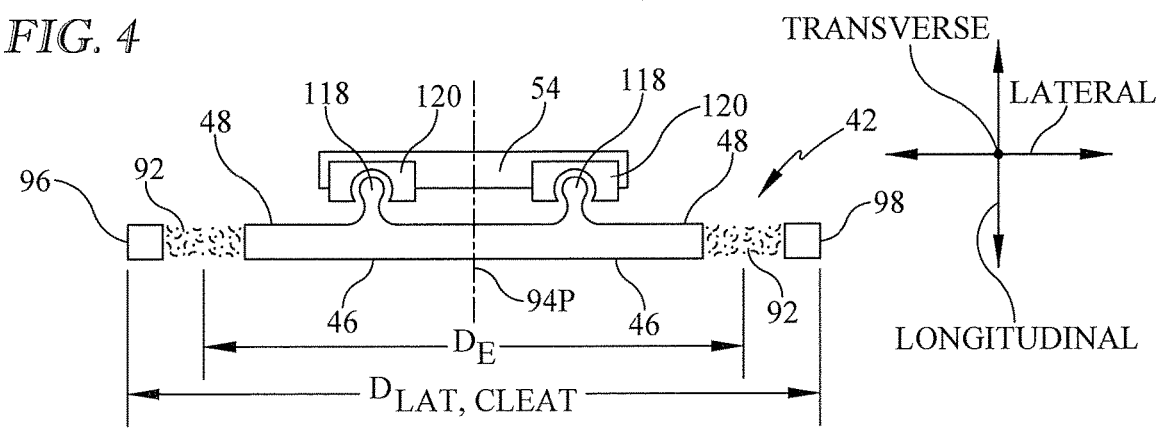
FIG. 5
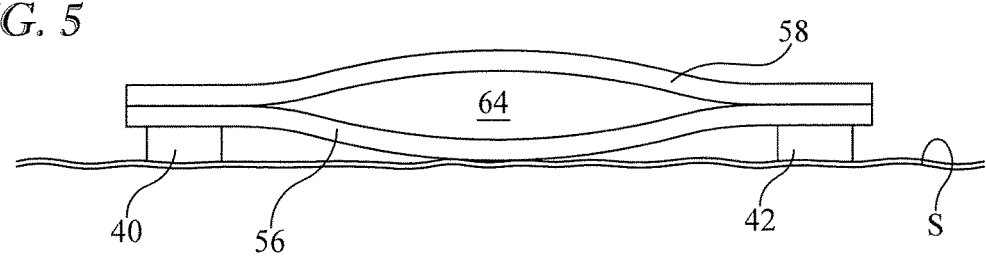
FIG. 5A
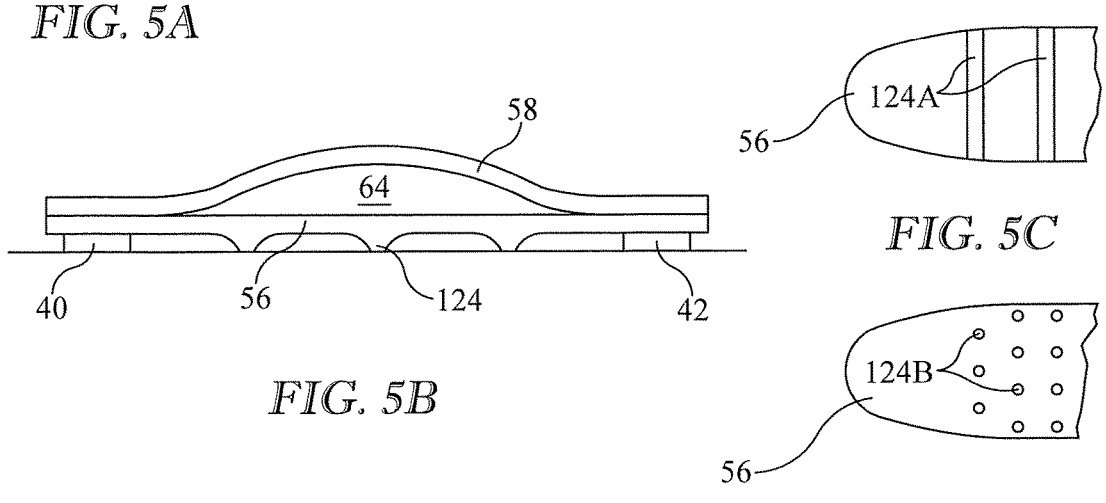
FIG. 5B
FIG. 5C
FIG. 5D

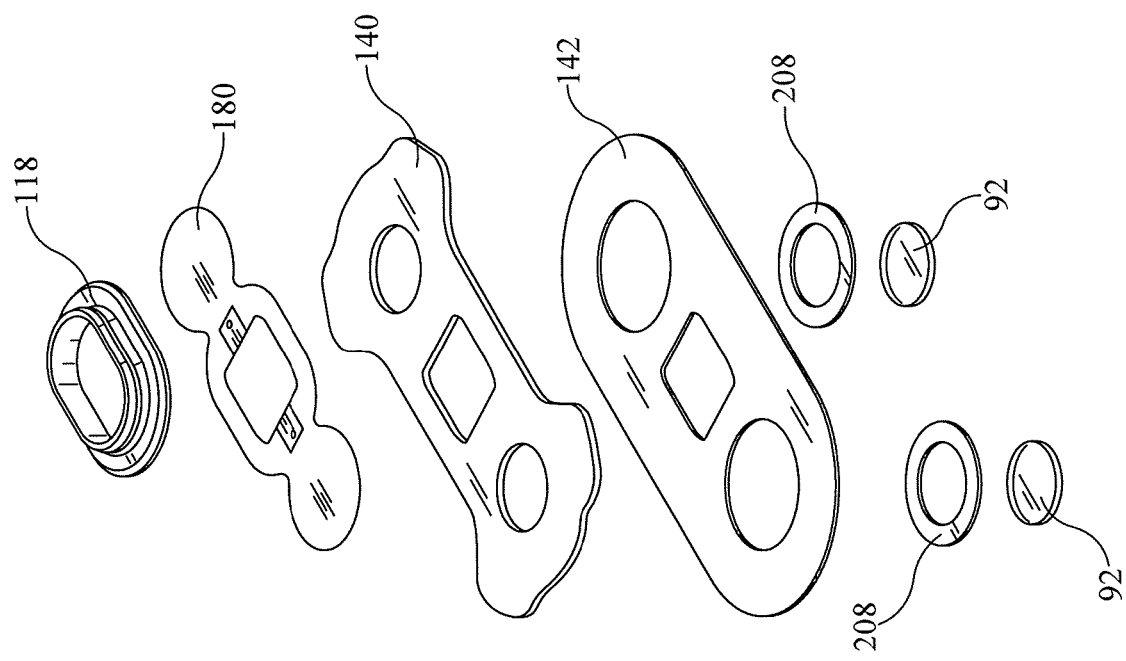

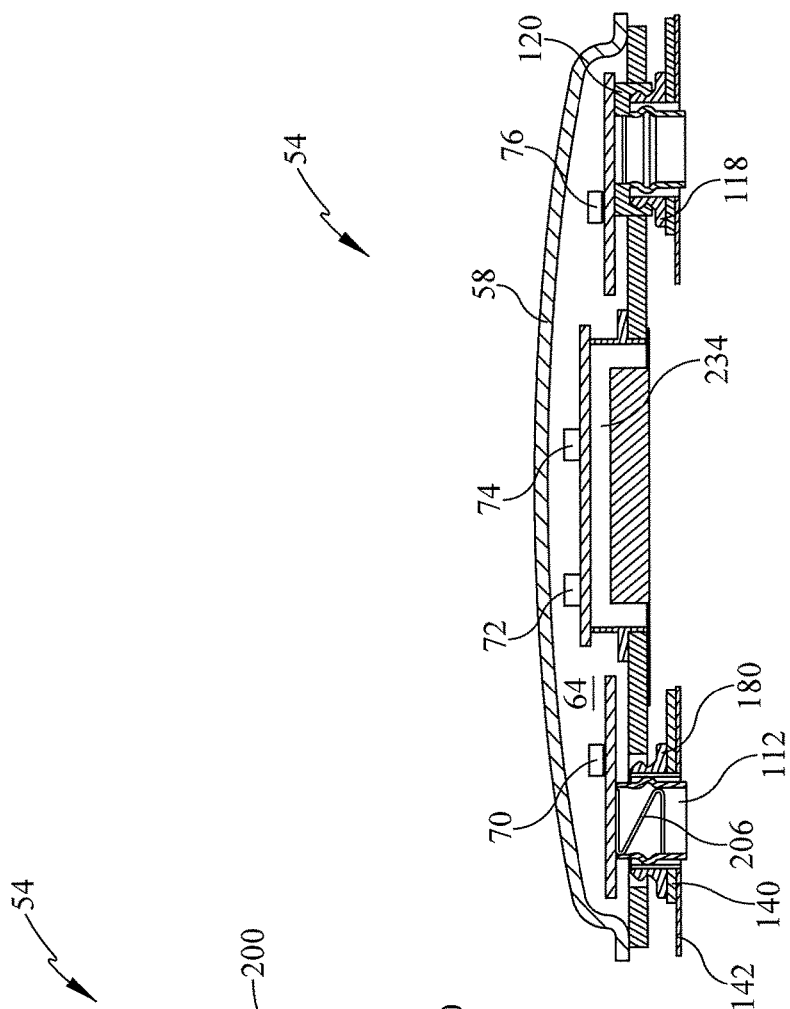
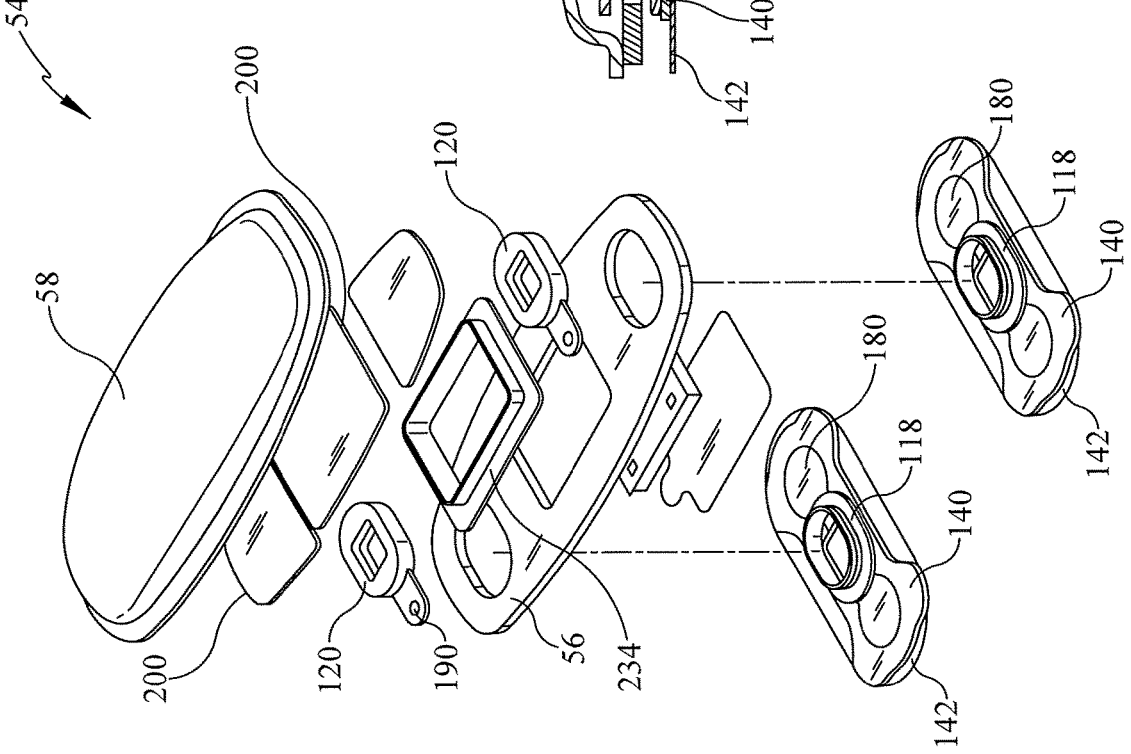

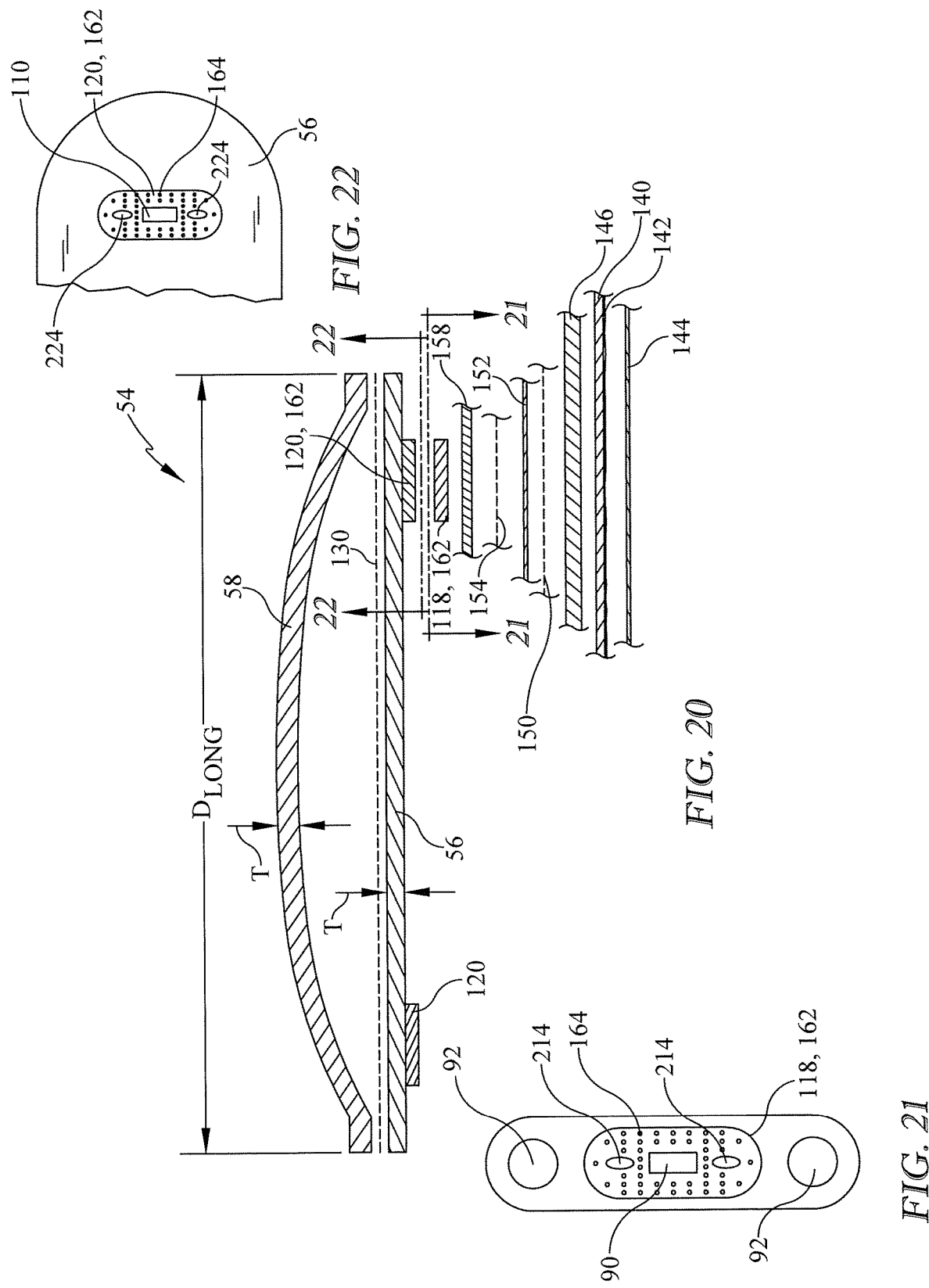

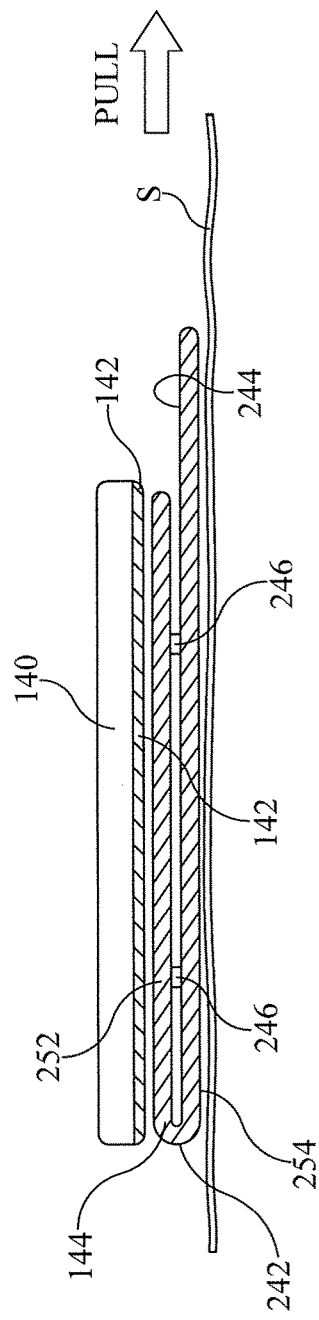
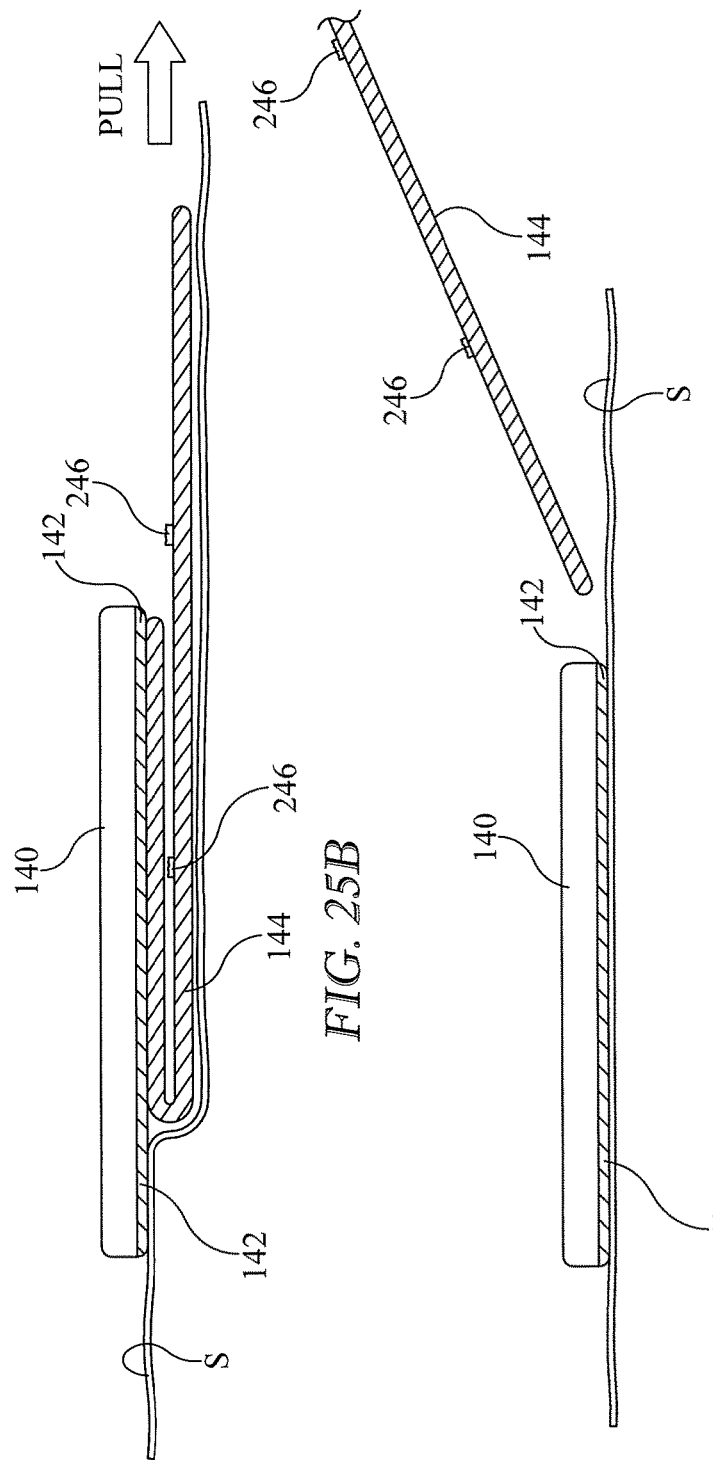
FIG. 25A
FIG. 25B
FIG. 25C

MODULAR VITAL SIGNS MONITOR

CROSS REFERENCE TO RELATED APPLICATIONS

This application claims priority to U.S. provisional applications 62/588,598 entitled "Modular Vital Signs Monitor" filed on Nov. 20, 2017, 62/592,602 entitled "Modular Vital Signs Monitor" filed on Nov. 30, 2017, and 62/618,772 entitled "Modular Vital Signs Monitor" filed on Jan. 18, 2018, the contents of all of which are incorporated herein by reference.

TECHNICAL FIELD

The subject matter described herein relates to medical vital signs monitors and particularly to a modular monitor having a module which is wearable by a subject (e.g. a medical patient) and a detachable module which is detachable from the wearable module. The detachable module can be detached from the monitor when the patient participates in activities which might be harmful to components of the detachable module. The detachable module can be subsequently reattached to the wearable module.

BACKGROUND

Wearable monitors for monitoring medical vital signs are advantageous because they can provide continuous monitoring of the vital signs of a subject, such as a hospital patient. Wearable monitors include an adhesive layer for securing the monitor to the patient. The adhesive layer is covered by a peel-off protective liner. A caregiver removes the liner to expose the adhesive and then presses the monitor against the patient's skin to secure the monitor to the patient's body.

One drawback of wearable monitors is the need to remove the monitor from the patient when the patient participates in activities that could cause damage to components of the monitor. Such activities include bathing, showering, and radiological procedures. At the conclusion of the activity a caregiver rescues the wearable monitor to the patient. However because it is difficult to position the monitor exactly as it had been before removal, the quality and/or consistency of the monitored signals may suffer. The monitor described herein overcomes at least this shortcoming of conventional vital signs monitors.

Another problem associated with wearable monitors is related to the initial positioning of the monitor on the patient. It is necessary to secure the monitor to a location on the patient's body that will enable its sensors to receive high quality signals from the patient's body. Either by experience or by consulting instructions, a caregiver knows the general region of the patient's body where the monitor should be secured. However the most suitable body location varies from patient to patient. In order to identify a satisfactory location for a particular patient the caregiver positions the monitor on or near the patient's body with the protective liner still covering the adhesive. The caregiver then adjusts the location of the monitor until its output signals indicate that the monitor is in a reasonably satisfactory location for acquiring clinically useful signals from the patient's body. The caregiver then lifts the monitor away from the patient in order to peel off the protective liner. But by doing so the caregiver may lose track of the identified satisfactory location. Selected embodiments of the monitor described herein overcome this problem.

SUMMARY

A vital signs monitor includes a subject wearable first cleat having a first sensor opening and a pair of laterally spaced apart first electrodes. The monitor also includes a subject wearable second cleat having a pair of laterally spaced apart second electrodes. An equipment housing is removably attached to or attachable to the first and second cleats. The housing has a first sensor pocket which registers with the first sensor opening. The monitor also includes a first sensor aligned with the first sensor opening and the first sensor pocket.

BRIEF DESCRIPTION OF THE DRAWINGS

The foregoing and other features of the various embodiments of the vital signs monitor described herein will become more apparent from the following detailed description and the accompanying drawings in which:

FIG. 4 is a schematic cross sectional view of a first cleat of FIG. 3.

FIG. 5 is a schematic cross sectional view of a second cleat of FIG. 3.

FIG. 5A is a schematic, cross sectional side elevation view of the vital sign monitor in which the base of the equipment module flexes enough to contact a patient's skin.

FIG. 5B is a view similar to that of FIG. 5A showing standoffs to regulate the area of contact between the base of the equipment module and the patient's skin.

FIG. 5C is view of a fragment of the patient side of an equipment module, such as that of FIG. 5B, in which the standoff feature is a set of ribs.

FIG. 5D is view of a fragment of the patient side of an equipment module, such as that of FIG. 5B, in which the standoff feature is an array of bumps.

FIGS. 15-17 are an exploded view, an assembled view, and a plan view of the cleat of FIG. 14.

FIG. 18 is an exploded view showing the cleats of FIGS. 14-17 in the context of an equipment housing which is similar to the housing of FIG. 7 but which includes an electronics component housing.

FIG. 19 is an assembled view of the cleats and housing of FIG. 18.

FIG. 20 is an exploded elevation view of another embodiment of a cleat shown in the context of the equipment housing of FIGS. 7-8.

FIG. 21 is a view in the direction 21-21 of FIG. 20 showing a cleat connector element.

FIG. 22 is a view in the direction 22-22 of FIG. 18 showing a housing connector element.

FIGS. 25A, 25B and 25C are a sequence of views of the cleat of FIG. 24 showing how the force of a caregiver's pull on a liner tab progressively releases the liner from the adhesive.

Features similar to or the same as features already described may be identified herein by the same reference numerals already used.

DESCRIPTION

Figure 1:
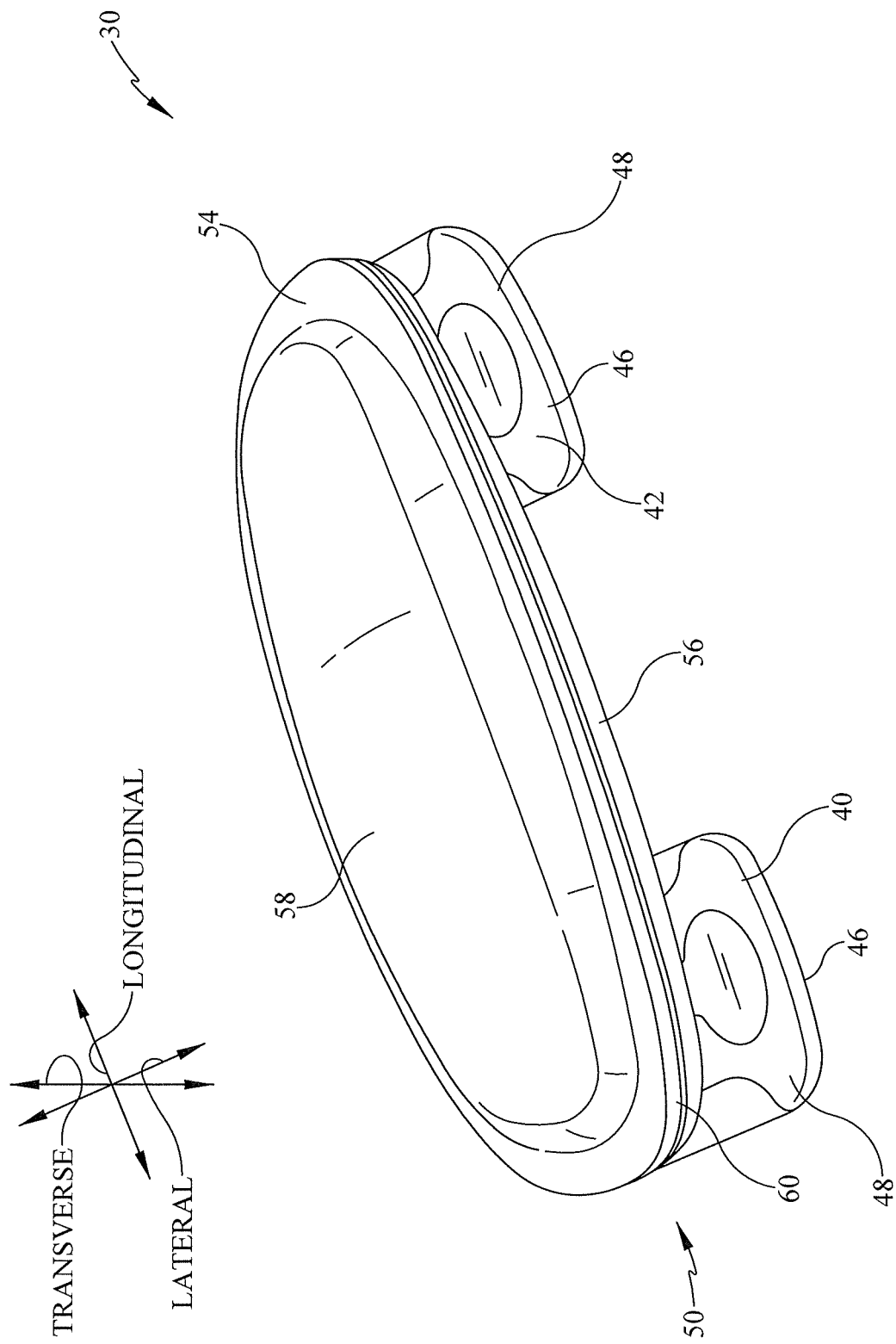
FIGS. 1 and 2 are views of a mockup of a vital signs monitor comprised of a pair of cleat modules and an equipment module.
Figure 2:
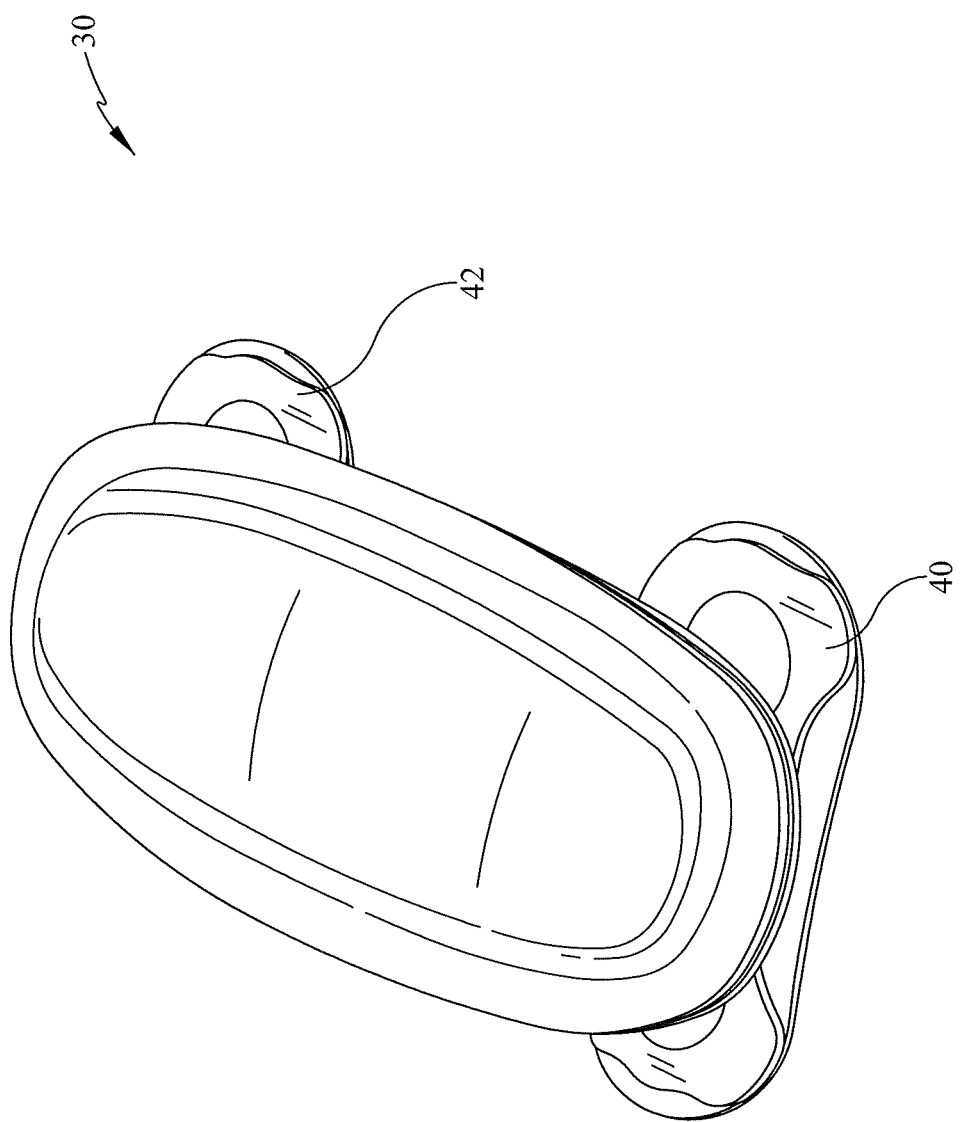

FIGS. 1-5 show a vital sign monitor 30 which is wearable by a subject such as a hospital patient. FIG. 1 also includes mutually orthogonal lateral, longitudinal and transverse reference axes. The monitor includes first and second cleat modules 40, 42, which are also referred to simply as first and second cleats. Each cleat has a subject facing side 46 and an environment facing side 48. The cleats are "subject wearable" in that they can be applied to a subject's skin, will resist unintentional dislodgement over a specified interval of time (e.g. five days) under conditions of normal use, but can be readily removed from the subject whenever required. The phrase "conditions of normal use" refers to the conditions that the cleat is likely to encounter during a hospital stay, and includes bathing, showering, and exposure to radiological procedures.

The monitor also includes an equipment module 50. Module 50 includes a housing 54 comprised of a base 56 and a cover 58 adhesively held to each other at a seam 60. The base and cover define an equipment compartment 64. The base is removably attached to (and detachable from) the first and second cleats as described in more detail below. "Removably attached" means that the housing can be detached from (and attached to) the cleats without the use of tools or equipment and with the exertion of only a modest force. In one example the housing is configured so that a caregiver can grasp it and manually separate it from the cleats, which remain in place on the patient's skin. "Removably attached" additionally means that the housing can be repeatedly attached to and detached from the cleats.

Equipment module 50 also includes electronic components of the monitor. The electronic components are housed in equipment compartment 64. The electronic components include at least a processor 70 for processing data signals which originate at electrodes and at sensors which are described in more detail below. The compartment may also house one or more amplifiers 72 and one or more filters 74 to amplify and de-noise the sensor and electrode signals. A transceiver 76 provides communication with remote devices such as information displays and user controls. The compartment also houses a battery 80. Collectively, the processor, amplifier, filter and transceiver are referred to as an electronics suite 82.

At least one of the cleats, such as first cleat 40, includes a first sensor opening 90 and a pair of laterally spaced apart electrodes 92. The portion of the cleat which coincides transversely with the electrode may be thought of as an electrode host. The illustrated electrodes are hydrogel electrocardiogram (EKG) electrodes, however may instead be other types of electrodes and/or electrodes used for reasons other than electrocardiography. The electrodes are on laterally opposite sides of a longitudinally extending reference line 94L or reference plane 94P. In the illustrated embodiment the reference line is a centerline which is the common longitudinally extending centerline of cleats 40, 42 and of equipment housing 54. Similarly the reference plane is a center plane which is the common longitudinally extending center plane of cleats 40, 42 and of equipment housing 54. The first sensor opening 90 of the illustrated embodiment is centered midway between the lateral ends 96, 98, of the cleat, and the first electrodes 92 are equally spaced from the first sensor opening on laterally opposite sides of the first sensor opening.

Second cleat 42 may or may not have a sensor opening. The illustrated second cleat does not have a sensor opening, but is otherwise the same as the first cleat. The second cleat has a subject facing side 46, an environment facing side 48, and a pair of laterally spaced apart second electrodes 92. The illustrated electrodes are hydrogel electrocardiogram (EKG) electrodes and are on laterally opposite sides of a longitudinally extending reference line 94L or reference plane 94P, but may instead be electrodes suitable for some other purpose. In the illustrated embodiment the reference line is a centerline of cleats 40, 42 and of housing 54. The illustrated reference plane is a center plane 94P, which is the longitudinally extending center plane of cleats 40, 42 and of housing 54. Second electrodes 92 are on laterally opposite sides of longitudinally extending reference line 94L and are equally laterally spaced therefrom.

Housing 54 includes a first sensor pocket 110 which registers with first sensor opening 90, and a first sensor 112 (illustrated schematically as a hexagon) aligned with the first sensor opening and the first sensor pocket. Taken together, the first sensor opening and first sensor pocket comprise a first sensor cavity, and the first sensor resides in the first sensor cavity. Specific example sensors include photoplethysmogram (PPG) sensors, phonocardiogram (PCG) sensors, and oxygen saturation (SpO2) sensors. To the extent that the sensor of interest is a component of a sensor system that relies on other system components (e.g. red and infrared light sources for a reflectance SpO2 sensor) those other system components may also reside in the sensor cavity. The first sensor cavity may include a single sensor or multiple sensors of the same or different types where "type" refers to the purpose of the sensor, e.g. PPG, PCG, SpO2.

Figure 6:
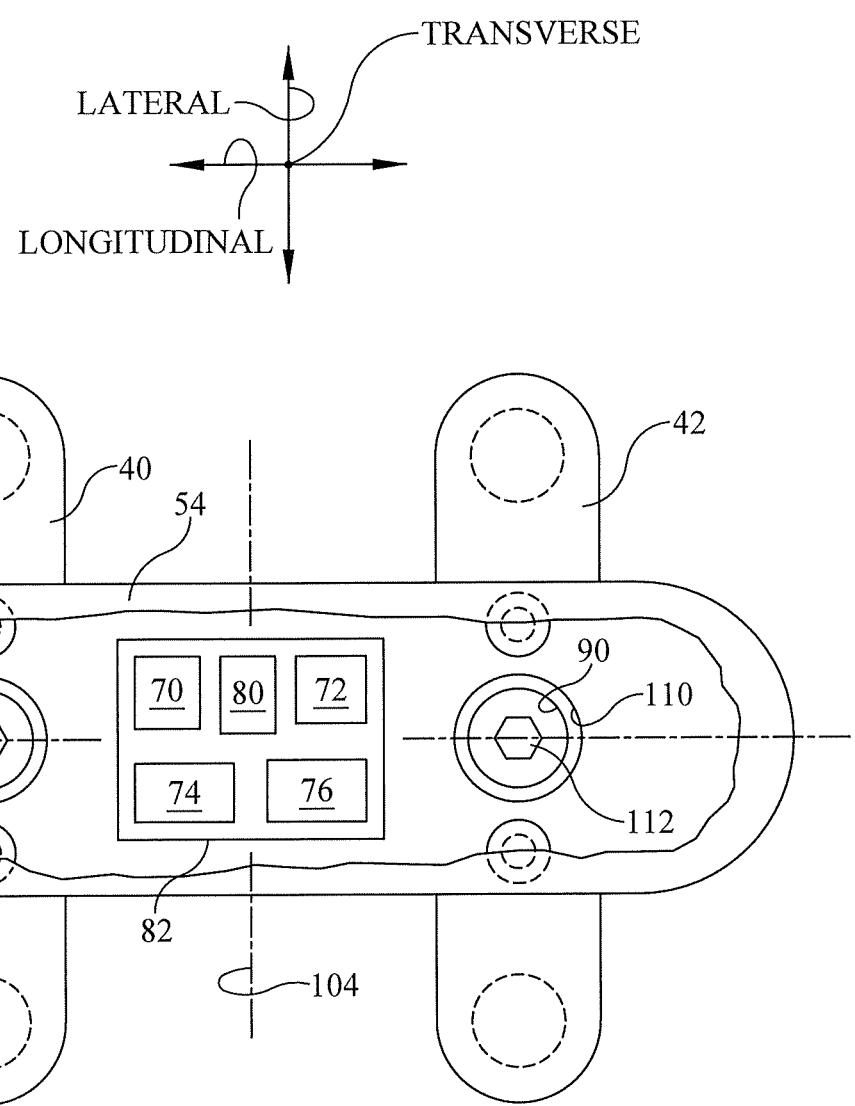
FIG. 6 is a view similar to that of FIG. 3 in which the equipment housing includes two sensor pockets, and each of the cleats includes a sensor opening in registration with one of the sensor pockets, and also showing a sensor associated with each registering pair of pockets and openings.

The illustrated vital signs monitor includes only a single sensor pocket and a single sensor opening. However the monitor may include a second sensor pocket 110 and a second sensor opening 90 which registers with the second sensor pocket as shown in FIG. 6. Taken together, the second sensor opening and second sensor pocket comprise a second sensor cavity. A second sensor 112 may reside in the second sensor cavity. The second sensor cavity may include a single sensor or multiple sensors of the same or different types. The sensor or sensors in the second cavity may all be the same type as those in the first sensor cavity, may all be different types, or may be a mix of same and different types. Alternatively the second sensor pocket may be left empty.

First cleat 40 includes a pair of first cleat connector elements 118. The first cleat connector elements are laterally offset from sensor opening 90 in laterally opposite directions. In the illustrated embodiment the first cleat connector elements are transversely projecting studs. Second cleat 42 includes a pair of second cleat connector elements 118. The second cleat connector elements are laterally offset from a longitudinally extending reference plane 94P of the second cleat in laterally opposite directions. In the illustrated embodiment the second cleat connector elements are transversely projecting studs.

The equipment housing includes housing connector elements 120. In the illustrated embodiment the housing connector elements are receptacles.

As seen best in FIGS. 4-5, equipment housing 54 is removably attachable to first and second cleats 40, 42 by way of a mating relationship between the cleat connector elements 118 and the housing connector elements 120. Each mating connector element pair defines a mechanical connection between the cleat and the housing. For example each mating stud 118 and receptacle 120 define a snap connection. The snap connection enables the housing to be repeatedly attached to and detached from the cleats without the use of tools or equipment and with the exertion of only a modest manual force.

As illustrated in FIGS. 1-5 and elsewhere, the patient facing side of the equipment housing is transversely offset from the patient's skin S. However if the cleat is sufficiently thin, and the housing base is sufficiently flexible, the housing may instead flex enough to lie against the patient's skin as seen in FIG. 5A. If contact between the housing and the patient's skin S is considered to be undesirable, the patient side of housing base 56 may include a standoff feature 124 as seen in FIG. 5B. One specific example of a standoff feature is the ribs 124A of FIG. 5C. Another example is the array of raised bumps 124B of FIG. 5D. The standoffs limit the area of contact between the housing and the patient's skin. One advantage of the housing of FIG. 5B in comparison to that of FIG. 5A is improved air circulation and air movement along the patient's skin.

Figure 7:
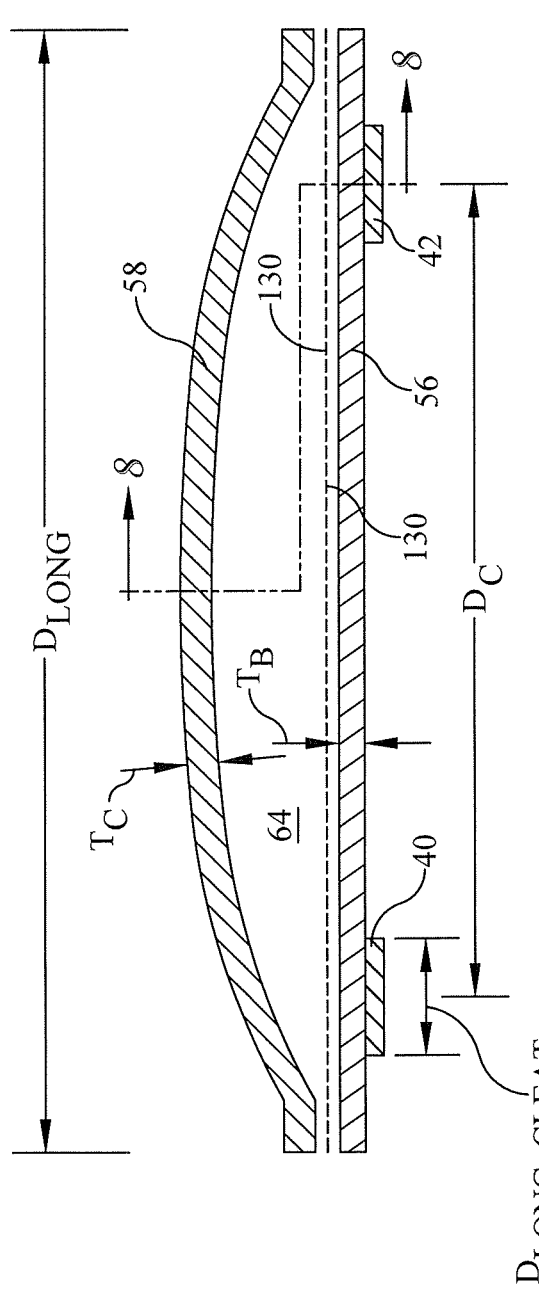
FIG. 7 is a schematic, exploded, cross sectional side elevation view of the equipment housing and the cleats of FIGS. 1-2.
Figure 8:
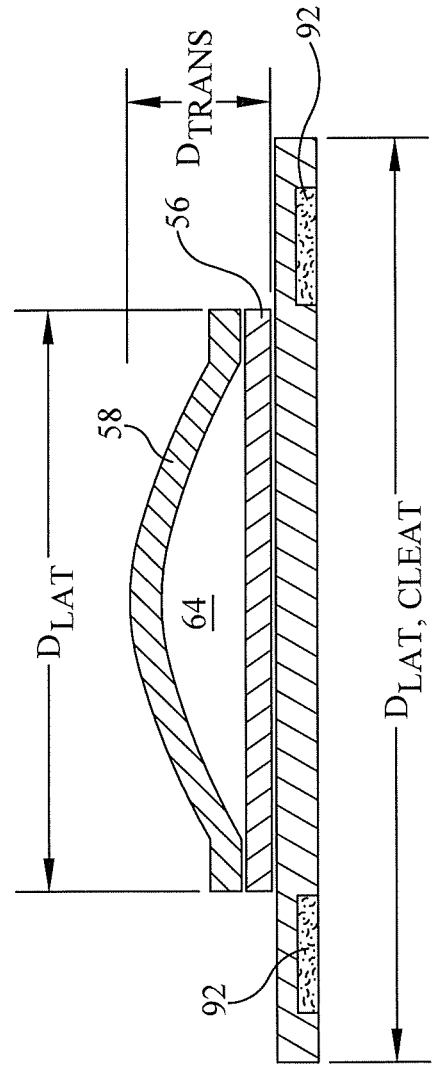
FIG. 8 is a schematic, nonexploded cross sectional end elevation view of the equipment housing and one of the cleats of FIG. 7.

Referring to FIGS. 7-8, in one embodiment the equipment housing is constructed as set forth below. The products indicated in parentheses are suitable products for the components of the housing, however other products may also be satisfactory. Moreover, the use of the same or similar reference numerals to identify analogous components of other embodiments of the housing elsewhere in this specification does not require that those other embodiments use the same products, nor does it guarantee that those products would be satisfactory for those other embodiments.

1) housing base 56 having a cross sectional profile which is predominantly linear or nearly so when viewed in the lateral direction, and a thickness $T_B$ of about 3 mm (FLEXTECH 6A foam; FLEXTECH products are manufactured by Flextech, Inc., 7300 W 27th St. St. Louis Park, Minn. 55426),
2) housing cover 58 having an arched profile in both the longitudinal and lateral directions and a thickness $T_C$ of about 3 mm (FLEXTECH L200 foam),
3) double sided adhesive 130 securing the base and cover to each other (3M 1510 double sided adhesive; the "3M" products referred to herein are manufactured by 3M, headquartered at the 3M Center, St. Paul, Minn., 55144-1000).

The FLEXTECH 6A foam is denser than the FLEXTECH L200 foam. The higher density of the FLEXTECH foam makes it stiff enough to provide suitable structural support for the electronics suite. The lower density FLEXTECH L200 foam is more flexible and therefore helps enhance patient comfort.

The housing has a longitudinal dimension $D_{LONG}$ of about 12 cm, a lateral dimension $D_{LAT}$ of about 6 cm and a transverse dimension $D_{TRANS}$ of about 1 cm.

Each cleat has a longitudinal dimension $D_{LONG,CLEAT}$ of about 3.3 cm and a lateral dimension $D_{LAT,CLEAT}$ of about 7 cm. The center-to-center lateral separation $D_E$ between the electrodes 92 of a given cleat is about 3.8-5.5 cm. The longitudinal separation $D_C$ between the first and second cleats is about 8.5-11 cm. Other separations may also be satisfactory, including those that result in a nonrectangular distribution of the electrodes. If the electrodes are EKG electrodes, satisfactory separations of the electrodes are those that result in a spatial distribution of the electrodes consistent with acquiring clinically useful electrocardiography signals.

Figure 10:
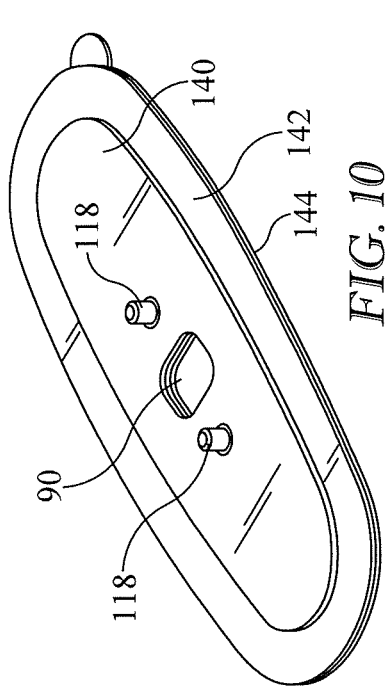
FIG. 10 is an assembled view of the cleat of FIG. 9 as seen from the environment side of the cleat.
Figure 11:
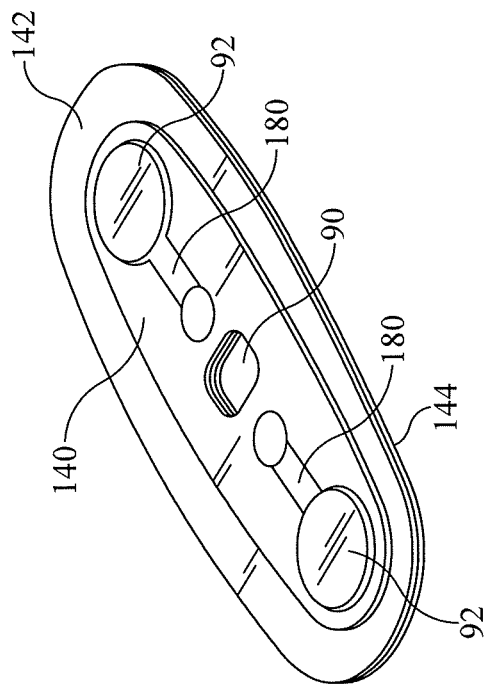
FIG. 11 is a view of the cleat of FIG. 10 in which a tape layer of the cleat has been shown as transparent in order render traces and electrode elements of the cleat visible to the observer.
Figure 9:
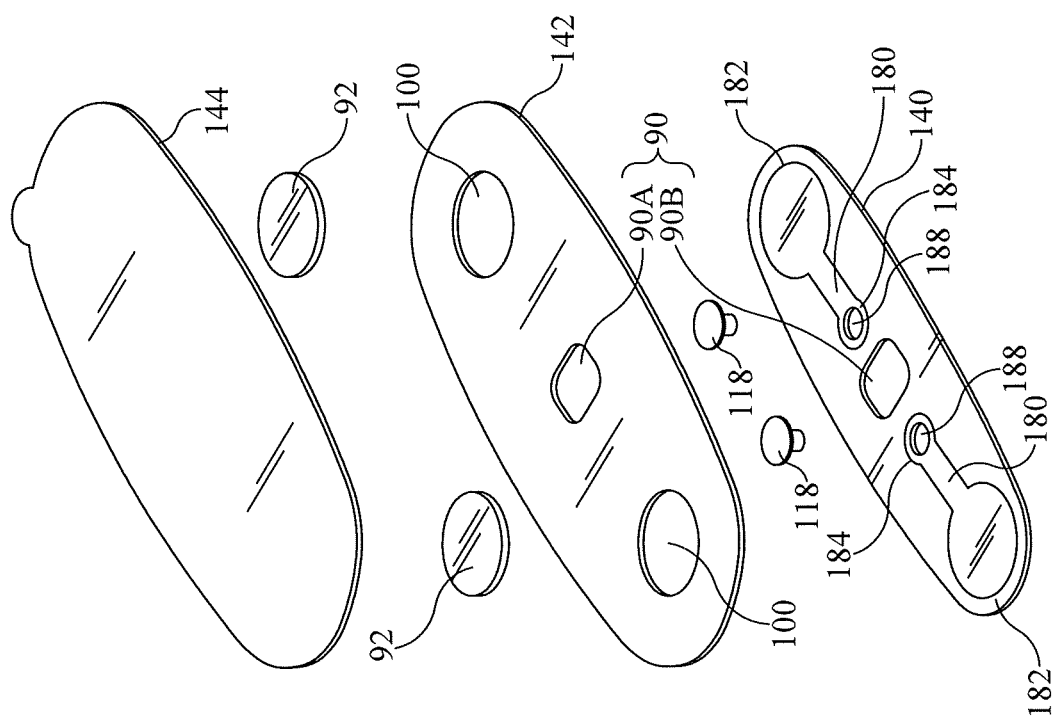
FIG. 9 is an exploded view of an embodiment of a cleat as seen from the patient side of the cleat.

FIGS. 9-11 are more detailed views of a cleat having cleat connector elements 118 such as those of FIGS. 4-5. FIG. 9 is an exploded view as seen from the patient side of the cleat. The cleat includes a tape layer 140, an adhesive layer 142, and a peel off protective liner 144. The protective liner covers the adhesive until a caregiver removes it prior to applying the cleat to a patient. An opening 90A and a pair of electrode openings 100 penetrate through layer 142. Each electrode opening receives an electrode 92. Tape layer 140 includes an opening 90B which registers with opening 90A. Openings 90A and 90B define a sensor opening 90. Tape layer 140 also includes a pair of printed electrically conductive traces 180 each having a larger diameter end 182 and a smaller diameter end 184. In one embodiment the traces are a silver-silver chloride (Ag—AgCl) ink. A hole 188 penetrates through the smaller end of each trace. The electrically conductive studs 118 extend transversely through holes 188.

FIG. 10 is an assembled view of the cleat of FIG. 9 as seen from the environment side of the cleat.

FIG. 11 is a view of the cleat of FIG. 10 in which tape layer 140 has been shown as transparent in order to make traces 180 and electrodes 92 visible to the observer.

Figure 12:
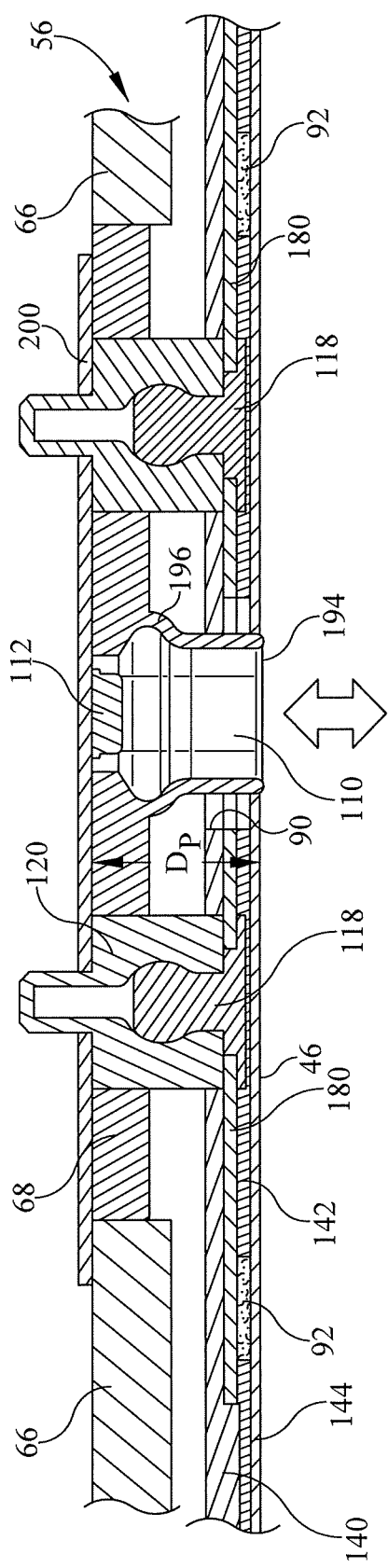
FIG. 12 is a cross sectional elevation view showing the cleat of FIGS. 9-11, a portion of an equipment housing removably attached to the cleat, and a sensor.
Figure 13:
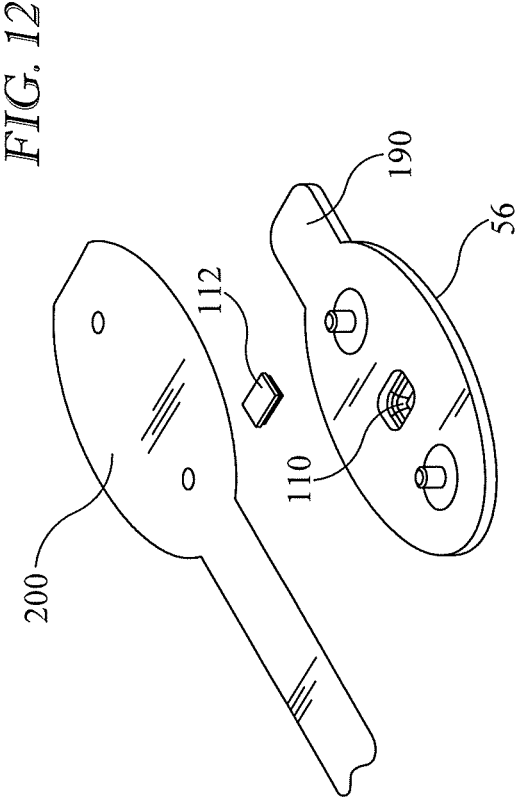
FIG. 13 is an exploded view showing the sensor and the portion of the housing of FIG. 12

FIG. 12 shows the cleat of FIGS. 9-11, a portion of an equipment housing 54 removably attached thereto, and a sensor 112 such as a PCG sensor. FIG. 13 is an exploded view showing the sensor and the portion of the housing of FIG. 12 The housing base 56 illustrated in FIGS. 12-13 has a foam portion 66 and a compression molded silicone portion 68 which includes sensor pocket 110 having a patient end 194, and a radially enlarged bellows-like portion 196. The compression molded silicone helps isolate sensor 112 to protect it from environmental contamination. Depending on the type of sensor, the environmental contaminants of concern may include moisture, light and noise. The compression molded silicone portion of the base includes a tab 190 which a caregiver can grasp to facilitate removal of the housing from the cleat. The housing includes a pair of receptacles 120 that mate with the cleat studs 118. Sensor 112, resides in the sensor cavity defined by sensor opening 90 and sensor pocket 110.

The sensor pocket has a transverse dimension $D_P$ large enough that when the housing is attached to the cleat as illustrated, the pocket projects transversely past the patient facing side 46 of the cleat. When the cleat is adhered to the patient by way of adhesive 142, contact between the patient and the patient end of the pocket compresses the bellows 196. The resultant reaction force from the bellows urges patient end 194 of the sensor pocket against the patient. The projecting character of the pocket and the reaction force attributable to the compressed bellows ensure that patient end 194 of pocket 110 remains in contact with the patient's skin even if the patient squirms or the adhesive 142 adheres imperfectly to the patient's skin or comes out of contact with the patient's skin.

Other sensors which may be installed in the sensor pocket may not require the patient end of the pocket to be in contact with the patient's skin. In those cases the pocket can be designed as a nonprojecting pocket without a bellows or similar feature.

Figure 3:
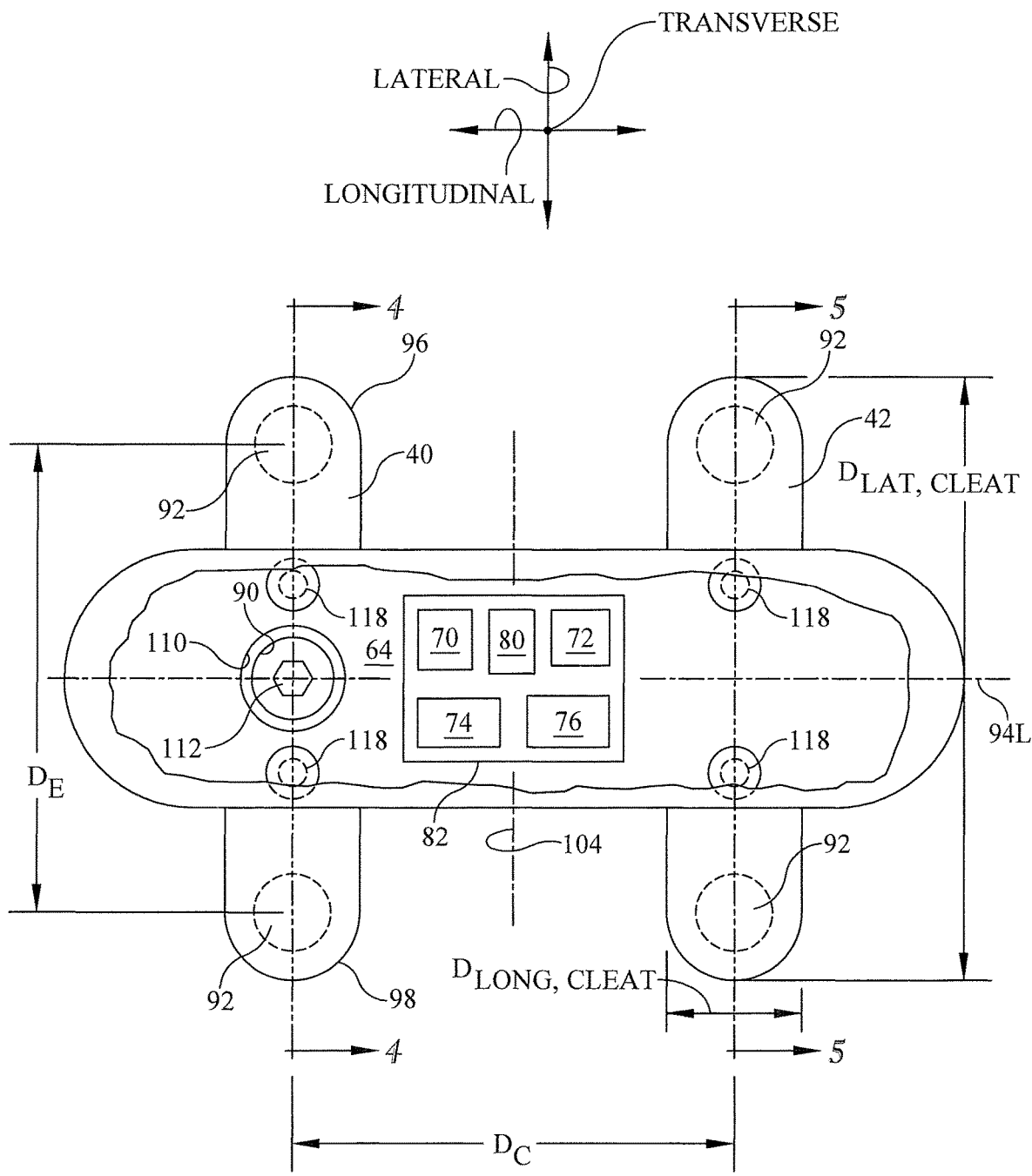
FIG. 3 is a schematic plan view of the cleats and equipment module of FIGS. 1 and 2 with a cover portion of the equipment module housing broken away to expose an internal equipment compartment, a sensor pocket of the housing, a sensor opening in the corresponding cleat, and an associated sensor.

A portion of a flexible circuit element 200 overlies the inner surface of housing base 56 and is in electrical contact with both the housing receptacles 120 and sensor 112. The flexible circuit element extends to the electronics suite 82 (FIGS. 3, 6). In operation, electrical signals from electrodes 92 follow a path along the corresponding traces 180, studs 118, and receptacles 120 and then to the flexible circuit element which conveys the signals to the electronics suite. Similarly, electrical signals from sensor 112 follow the circuit element to the electronics suite. (Alternatively the components of the monitor could be spatially arranged so that the electrical signals from the electrode and sensors do not require the presence of the circuit element 200.) As a result, the mated connector elements define not only a mechanical connection between the cleat and the housing, but also an electrical connection between the cleat and the housing. Accordingly, the combination of studs 118 and receptacles 120 may be thought of as members of an electrical connector assembly. Cleat electrical connector members 118 convey signals detected by the electrodes to electrical components of equipment module 50, including receptacles 120. Similarly, housing electrical connector members 120 receive signals from electrical components of the cleat, including studs 118.

Figure 14:
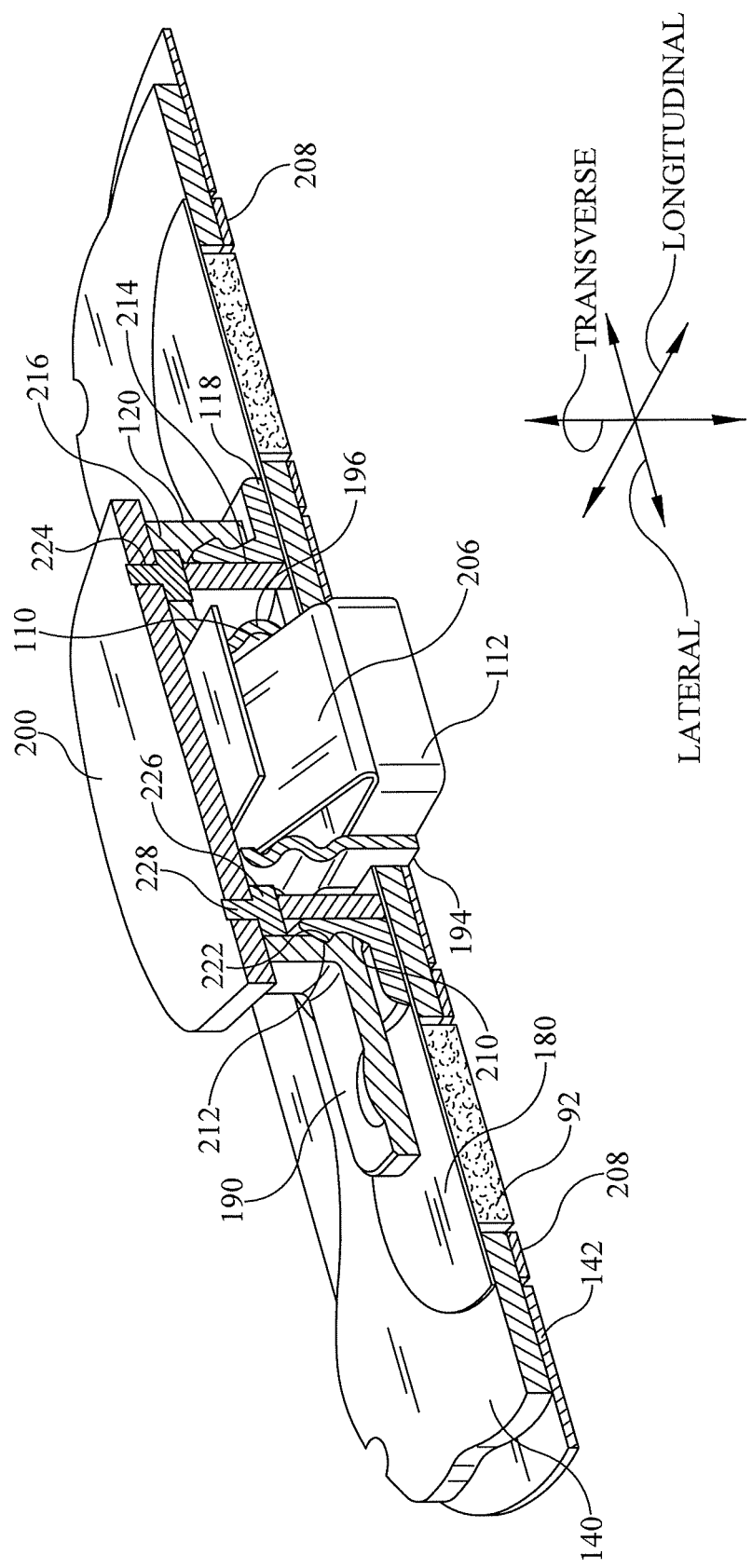
FIG. 14 is a cutaway view of another embodiment of a cleat and selected portions of a compatible equipment housing.

FIGS. 14-17 show another embodiment of a cleat and a portion of an equipment housing. In contrast to embodiments of the monitor in which each cleat has a pair of cleat connector elements and the equipment housing has a corresponding pair of housing connector elements for each pair of cleat connector elements (as seen for example in FIGS. 3-6, 9-10 and 12-13) the cleat of FIGS. 14-17 has exactly one cleat connector element 118. As seen best FIGS. 18-19, which show an equipment housing very similar to that of FIGS. 14-17, the base of the equipment housing has first and second housing connector elements 120, i.e. exactly one housing connector element 120 for each cleat to which the housing is to be connected. FIG. 14 also shows a representative sensor 112, a portion of a flexible circuit element 200, and a sensor conductor member 206 interposed between sensor 112 and flexible circuit element 200. The embodiment of FIGS. 14-17 also includes a gasket 208 circumscribing each electrode 92 to resist desiccation of the electrodes.

Figure 17:
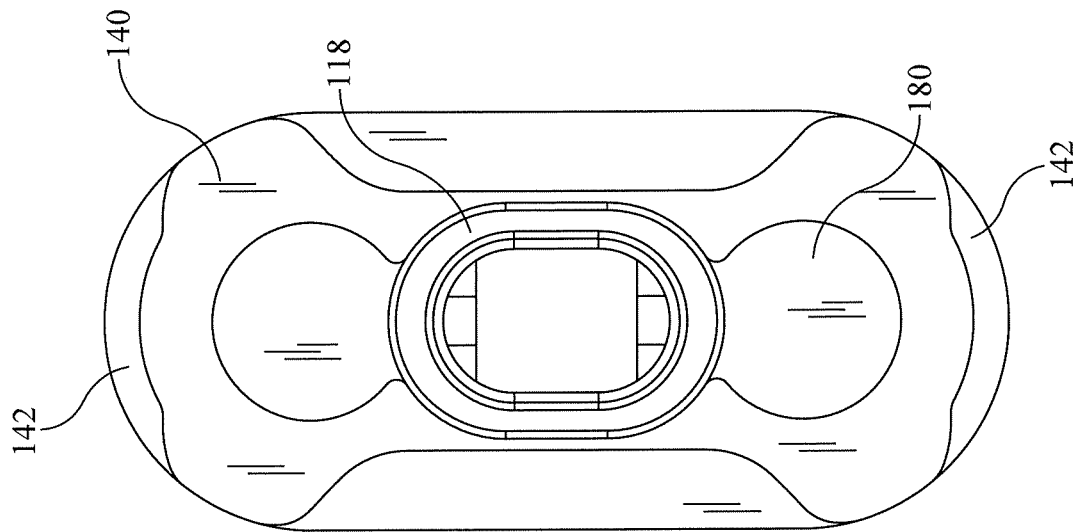
Figure 16:
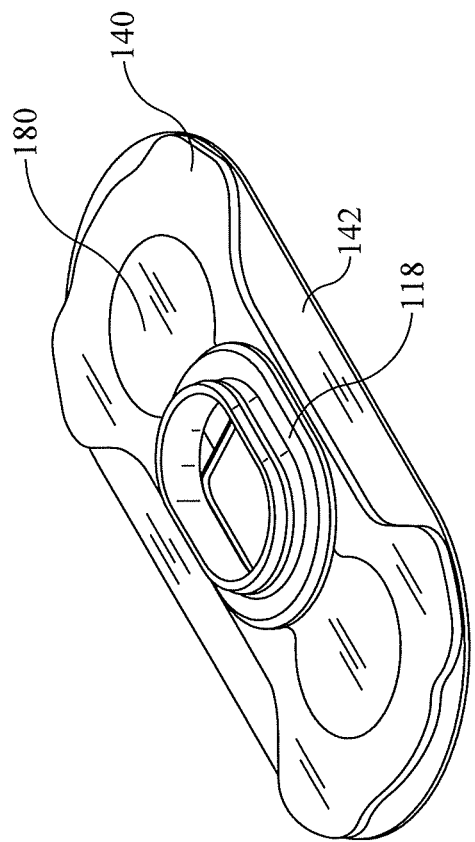

The cleat connector element of FIGS. 14-17 is a nonconductive ring which, in the illustrated embodiment, has a racetrack shaped planform (FIG. 17). Wall 210 of the element includes a perimetrical barb 212. Wall 210 circumscribes a pair of cleat conductive members 214 (illustrated only in FIG. 14) which extends transversely along the inner surface of wall 210. Cleat conductive members 214 are analogous to cleat electrical connector members 118 of previously described embodiments in that members 214 and members 118 play the role of the cleat side of a cleat-to-housing electrical connection.

The housing connector element 120 is a ring having an outer wall 216 with a perimetrical notch 222. A pair of conductive silicone members 224 are insert molded as part of the connector element. Each housing conductive member 224 has a base 226 and a post 228. The post extends into flexible circuit element 200. Wall 216 of housing connector element 120 circumscribes housing electrical conductive members 224. In particular wall 216 circumscribes bases 226 of housing electrical conductive members 224. Housing conductive members 224 are analogous to housing electrical connector members 120 of previously described embodiments in that members 224 and members 120 play the role of the housing side connector of a cleat-to-housing electrical connection.

When a caregiver presses connector element 118, 120 against each other the walls of the connector elements deflect so that barb 212 engages notch 222 to make a mechanical connection between the cleat and the equipment housing. Each mating cleat and housing connector element pair is configured so that the mating relationship between the housing and a given one of the cleats establishes both a cleat-to-housing mechanical connection and an electrical connection between the electrical elements of the given cleat and electrical elements associated with the housing. In particular, the bases 226 of the housing conductive members 224 contact the corresponding cleat conductive members 214 to make the electrical connection between the cleat and the housing. Conductive members 214 and 224 may be thought of as members of an electrical connector assembly. Cleat electrical conductive members 214 convey signals detected by the electrodes to electrical components of equipment module 50, including housing conductive members 224. Similarly, housing electrical conductive members 224 receive signals from electrical components of the cleat, including cleat conductive members 214. In addition sensor conductor member 206 comes into contact with flexible circuit element 200.

Electrical signals from electrodes 92 are conveyed to the electronics suite 82 (FIGS. 3, 6) by traces 180, cleat conductive members 214, housing conductive members 224 and flexible circuit element 200. Electrical signals from sensor 112 are conveyed to the electronics suite 82 by sensor conductor member 206 and flexible circuit element 200.

FIGS. 18-19 show the cleats of FIGS. 14-17 in the context of an equipment housing 54. The equipment housing illustrated in FIGS. 18-19 is similar to that of FIG. 7, but also includes an electronics component housing 234 which circumscribes the electronics suite (not illustrated) and battery (also not illustrated). On the left of FIG. 19 housing connector element 120 is not shown in order to reveal a sensor conductor member 206.

FIGS. 20-22 show another embodiment of a cleat in the context of an equipment housing 54. The cleat includes the layers set forth below. The 3M products indicated in parentheses are suitable products for the components of the housing, however other products may also be satisfactory. Moreover, the use of the same or similar reference numerals to identify analogous layers of other embodiments of the cleat elsewhere in this specification does not require that those other embodiments use the same products, nor does it guarantee that those products would be satisfactory for those other embodiments.

1) a first tape layer 140 (3M 1776 nonwoven tape),
2) adhesive 142 to secure the cleat to the patient's skin,
3) a protective peel-off liner 144 which a user peels off the adhesive before applying the cleat to the patient,
4) a second 1.5 mm thick foam tape layer 146 (3M 1772 foam tape),
5) a layer 150 of double sided adhesive (3M 1510 double sided adhesive),
6) a 0.13 mm polyester layer 152,
7) a second layer 154 of double sided adhesive (3M 1510 double sided adhesive), and
8) a 1.5 mm thick acrylic layer 158.

Figure 23:
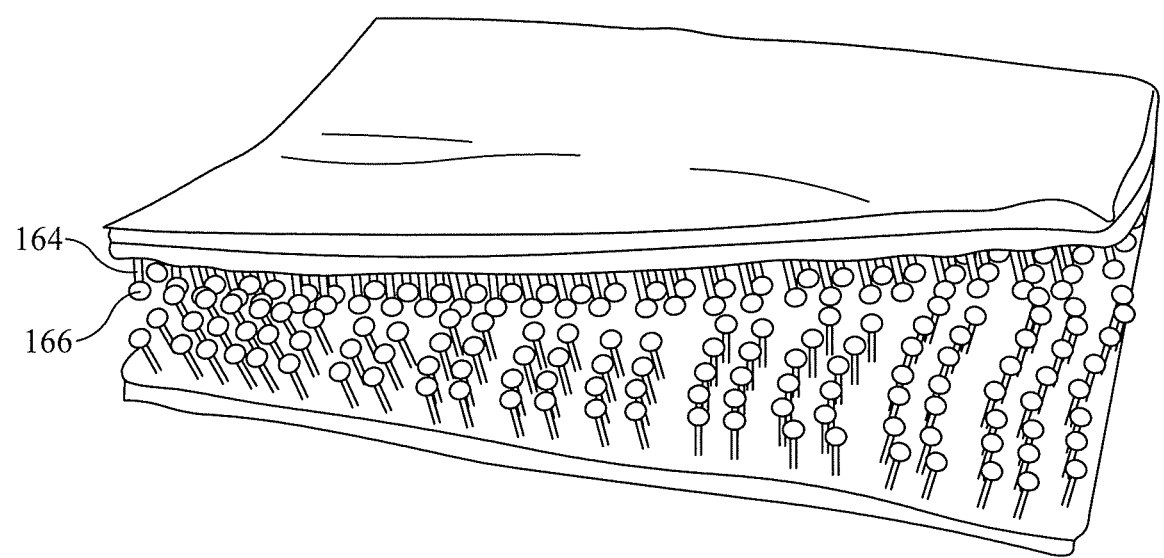
FIG. 23 is a view of a material used in the cleat connector element and housing connector element of FIGS. 20-22.

Referring additionally to FIG. 23, the cleat connector elements 118 and the housing connector elements 120 of FIGS. 20-22 are local patches 162 of a material known as duralock. The duralock material includes an array of slender pedestals 164 each of which has an enlarged head 166. A mating relationship between opposing duralock connector elements causes the equipment housing to be removably attachable to the cleats. Unlike the embodiments of FIGS. 3-6, 9-10, and 12-13, and like the embodiment of FIGS. 14-17, each cleat of FIGS. 20-22 has only a single cleat connector element, and the housing base has only two housing connector elements, one for each cleat. Referring to FIG. 21, the cleat includes cleat conductive members 214 and a sensor opening 90. Referring to FIG. 22, base 56 of the equipment housing module 54 includes housing conductive members 224 and a sensor pocket 110.

As noted in the Background section of this application, a caregiver needs to identify a location on the patient's body that will be clinically satisfactory for the monitor. To do so the caregiver positions the monitor on or near the patient's body with the protective liner 144 still covering the adhesive layer 142. The caregiver adjusts the location of the monitor until its output signals indicate that the monitor is in a reasonably satisfactory location. However when the caregiver lifts the monitor away from the patient in order to peel off the protective liner, he may lose track of the identified satisfactory location.

Figure 24:
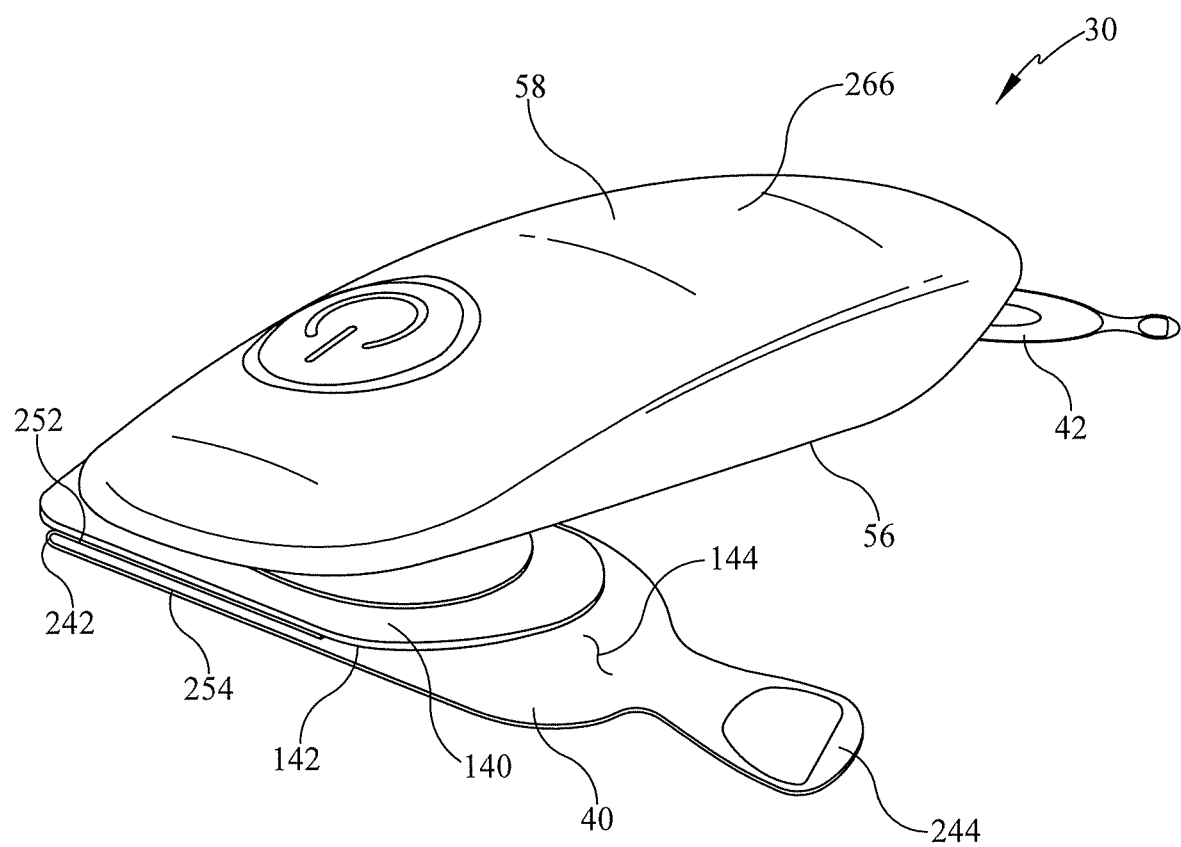
FIG. 24 is a view of a vital signs monitor whose cleats include a folded protective liner covering an adhesive layer of the cleats.
Figure 26:
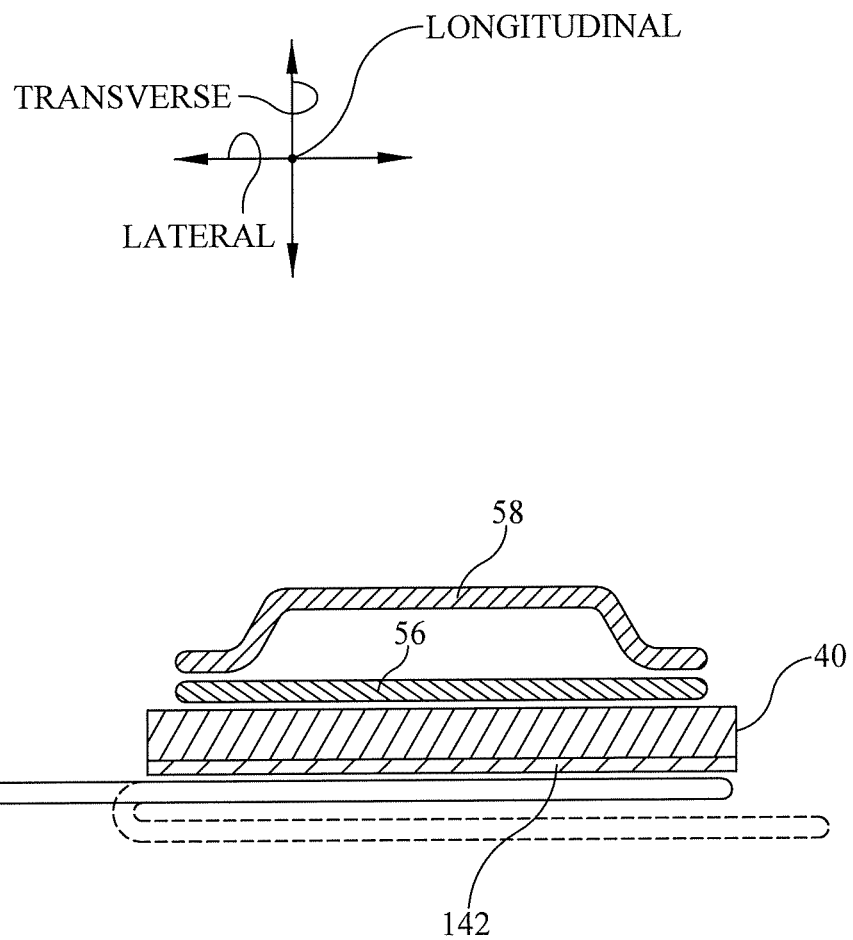
FIG. 26 is schematic, cross sectional view of a cleat similar to that of FIG. 24 showing an unfolded protective liner covering an adhesive layer of the cleat.

FIGS. 24-26 show an embodiment of a monitor 30 which addresses the above problem. The monitor includes a pair of cleats 40, 42 each having a substrate layer such as tape layer 140, an adhesive layer 142 and a protective liner 144 covering the adhesive. The protective liner includes a fold or crease 242 (FIGS. 24, 25A, 25B, 25C) and a tab 244. The liner may include a feature to maintain it in its folded state until the caregiver is ready to remove it. One such feature is a weak adhesive 246 connecting first and second portions 252, 254 of the liner which are on opposite sides of the fold. The first portion is in contact with the adhesive. The second liner portion is separated from the adhesive by the first liner portion. The first liner portion is interposed between the second liner portion and the adhesive. Alternatively, the liner may be a nonfolded element as seen in FIG. 26, in which case the caregiver folds or creases the liner (as seen in phantom) before placing the monitor on the patient and adjusting its position to establish a satisfactory location for attachment to the patient.

As described above the caregiver adjusts the location of the monitor on the patient's body until he is satisfied with its output signals. The suitability of the output signals may be assessed in at least two ways. In one embodiment the monitor includes an on-board indicator such as a line of light emitting diodes (LED's) 258. The suitability of the clinical output signals is indicated by the quantity of illuminated LED's. Another way is to employ a suitability indicator on an off-board piece of equipment that communicates with the monitor. One such piece of equipment is the Connex® Vital Signs Monitor (CVSM) which is available from Welch Allyn, 4341 State Street Rd, Skaneateles Falls, N.Y. 13153.

Once the caregiver is satisfied with the location of the monitor on the patient's body, he holds the monitor against the patient's skin instead of following the conventional practice of lifting it away from the patient. The caregiver then pulls on tab 244 while holding the monitor stationary against the patient. The force of the caregiver's pull breaks the weak adhesive 246 (if present) and progressively releases the liner from the adhesive as seen in the sequence of views of FIGS. 25A-25C. The adhesive exposed by peeling away the liner adheres the cleat, and therefore the monitor, to the patient's skin.

Figures 27, 28:
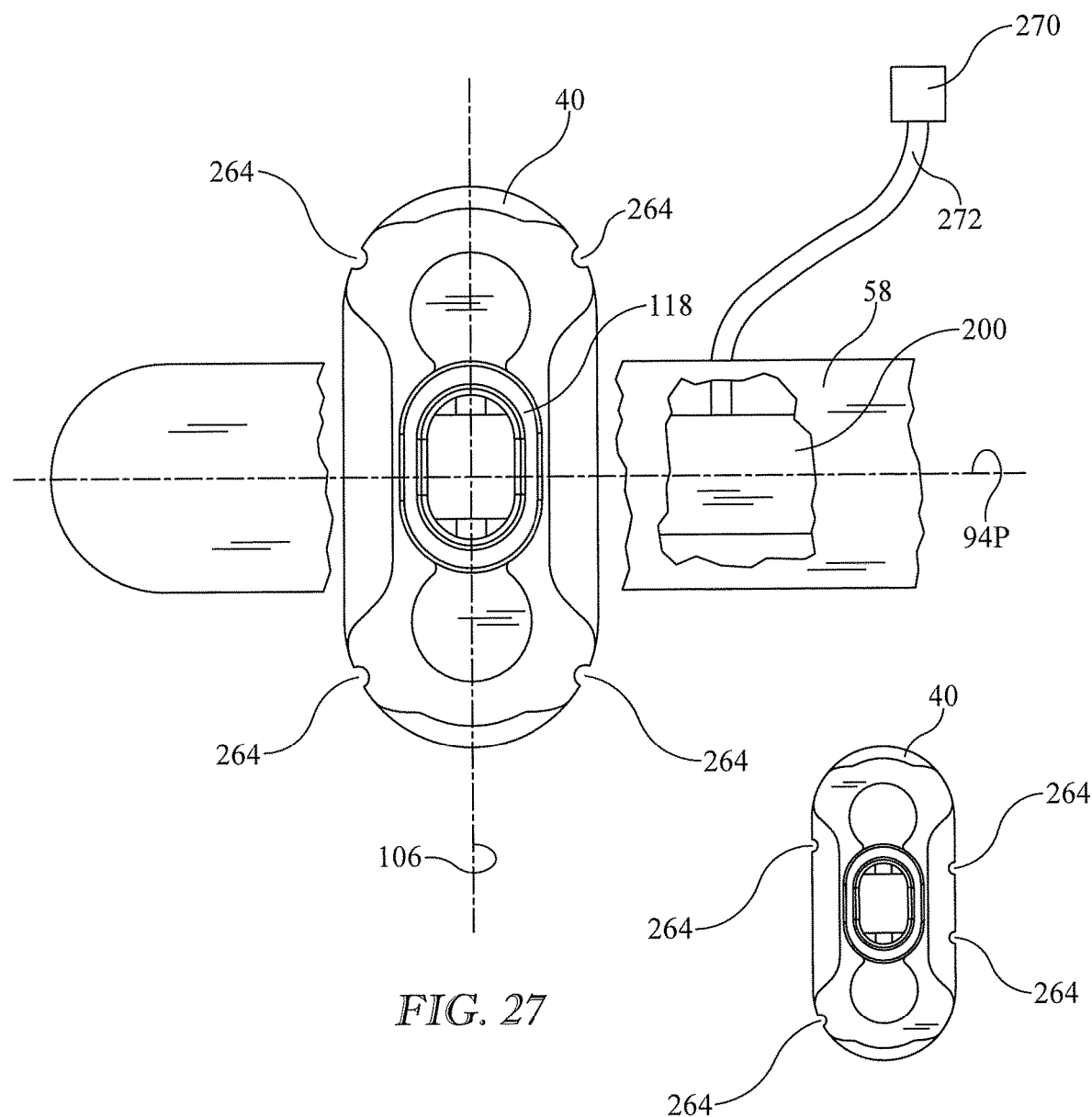
FIG. 27 is a plan view of a cleat having registration notches arranged in a first configuration.
FIG. 28 is a plan view of a cleat having registration notches arranged in a second configuration.

FIG. 27 shows another cleat embodiment similar to the cleats of FIGS. 16-19. The cleat includes a registration feature such as registration notches 264. Once the caregiver has identified a satisfactory position for the monitor to be adhered to the patient's skin, he uses a marker to mark the patient's skin at two or more of the notches. The caregiver then lifts the monitor away from the patient, peels off the protective liner, and then presses the monitor, with the adhesive now exposed, firmly against the patient's skin so that the notches coincide with the previously made marks.

The notches of FIG. 27 are located symmetrically on the cleat relative to planes 94P and 106. Alternatively the notches can be arranged in a way that will guard against caregiver confusion about the intended orientation of the monitor. One such arrangement is the nonsymmetrical notch arrangement of FIG. 28.

FIG. 27 also shows that the various embodiments of the monitor may include one or more satellite sensors or electrodes 270. A satellite sensor is a sensor that does not fall within the planform of the cleats and equipment housing. The satellite sensor is joined to equipment module 50 by a tether 272. The tether serves as a mechanical connector between sensor 270 and the equipment module. The illustrated tether extends to circuit element 200 to indicate that the tether may also serve as an electrical connector between sensor 270 and the equipment module. If the tether does not serve as an electrical connector, sensor 270 may communicate wirelessly with the components of the equipment module.

Although this disclosure refers to specific embodiments, it will be understood by those skilled in the art that various changes in form and detail may be made without departing from the subject matter set forth in the accompanying claims.

FIGS. 29-38 illustrate a single cleat embodiment of the vital signs monitor. The embodiment is referred to as "single cleat" because it employs only one cleat to adhere the monitor to a patient's skin.

Referring principally to FIGS. 29-34, the monitor includes an equipment module 50. The equipment module includes a housing 54 comprised of a base 56 and a cover 58 held to the base by, for example, an adhesive. The housing has an environment facing side 280 and a subject or patient facing side 282. The phrase "subject facing side" is used to distinguish side 282 from environment facing side 280 and does not require that side 282 actually be exposed to or in contact with the patient. Housing base 56 and housing cover 58 each have a planform in the lateral/longitudinal plane defined by their respective perimeters. The two planforms are common, i.e. they are line-on-line and define the planform of the housing.

The housing also includes a sensor receptacle 290 which projects transversely outwardly from the patient facing side 282 of the housing. The sensor receptacle has a wall portion 292 with an inner end 294 and an outer end 296. The illustrated sensor receptacle also includes a cover portion 302. The sensor receptacle may be monolithic in the sense of being formed or composed of material without joints or seams. Alternatively cover portion 302 may be a distinct element such as a film applied to the wall. Either way, housing base 56, housing cover 58 and receptacle 290 cooperate with each other to define a sealed equipment compartment 64. The sealed nature of the equipment compartment resists ingress of contaminants. Contaminants of concern may include moisture, all or selected frequencies of electromagnetic radiation, and all or selected noise frequencies. In another alternative the cover portion is absent. A noncovered receptacle may be required to accommodate sensors whose operation would be impaired by the presence of a cover.

Electronic components such as those already described in connection with the multiple cleat embodiments occupy the equipment compartment. The sensor receptacle 290 is part of the compartment 64 and houses one or more sensors 112 illustrated generically and schematically as a hexagon. Example sensors include photoplethysmogram (PPG) sensors, phonocardiogram (PCG) sensors, and oxygen saturation (SpO2) sensors.

The monitor also includes a single subject wearable cleat 44. The cleat has a subject or patient facing side 46 and an environment facing side 48. As with previously described embodiments, "environment facing side" is used to distinguish side 48 from patient facing side 46 and does not require that side 48 be exposed to the environment.

Cleat 44 includes a transversely outermost contact layer 310. Layer 310 is referred to as a contact layer because it is the layer adhered to and in contact with the patient's skin. In one embodiment contact layer 310 is comprised of a nonwoven fabric. The nonwoven fabric is adapted to allow moisture transport toward the perimeter of the contact layer. As a result, when the cleat is worn by a patient, the patient's perspiration can migrate laterally and longitudinally toward the perimeter of the nonwoven fabric layer and discharge into the environment.

Figure 29:
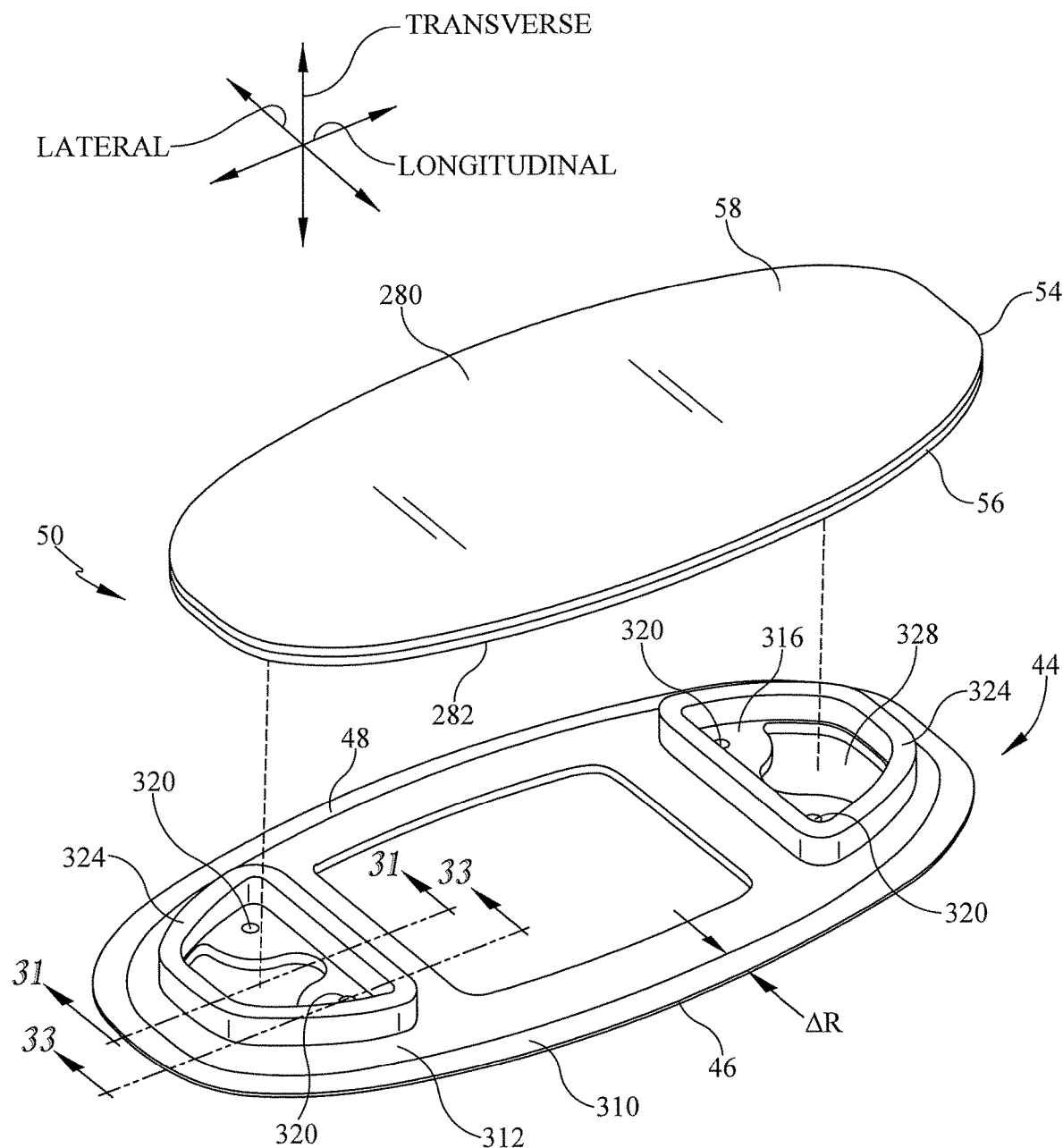
FIG. 29 is a view of a single cleat embodiment of a vital signs monitor having a cleat and an equipment housing, viewed from the equipment housing side of the monitor and showing the housing separated from the cleat.

The nonwoven fabric is adherable to the patient's skin. The nonwoven fabric may be inherently adhesive or may be provided with the property of adhesability by, for example, the application of an adhesive coating during manufacture. The adhesive is strong enough to secure the cleat to the patient's skin, but weak enough to enable the cleat to be removed without causing undue discomfort to the patient. The contact layer has a planform in the longitudinal/lateral plane which defines the planform of the cleat. The contact layer planform has a circumferentially varying radius $R_{CL}$ which is larger than the circumferentially varying radius $R_H$ of the equipment housing. When the housing is attached to the cleat the contact layer projects radially beyond the housing by a circumferentially uniform amount $\Delta R = R_{CL} - R_H$ (FIG. 29). Alternatively the contact layer planform and the housing planform may be the same so that when the housing is attached to the cleat the two planforms are line-on-line.

Cleat 44 also includes a backing layer 312 secured to the contact layer. The backing layer provides the cleat with a degree of rigidity which nonwoven fabric does not possess. However the backing layer is nevertheless flexible enough that the cleat will not easily separate from the patient's skin due to influences such as curvature of the patient's body or squirming or other movement of the patient. The backing layer has a planform in the longitudinal/lateral plane.

Figure 30:
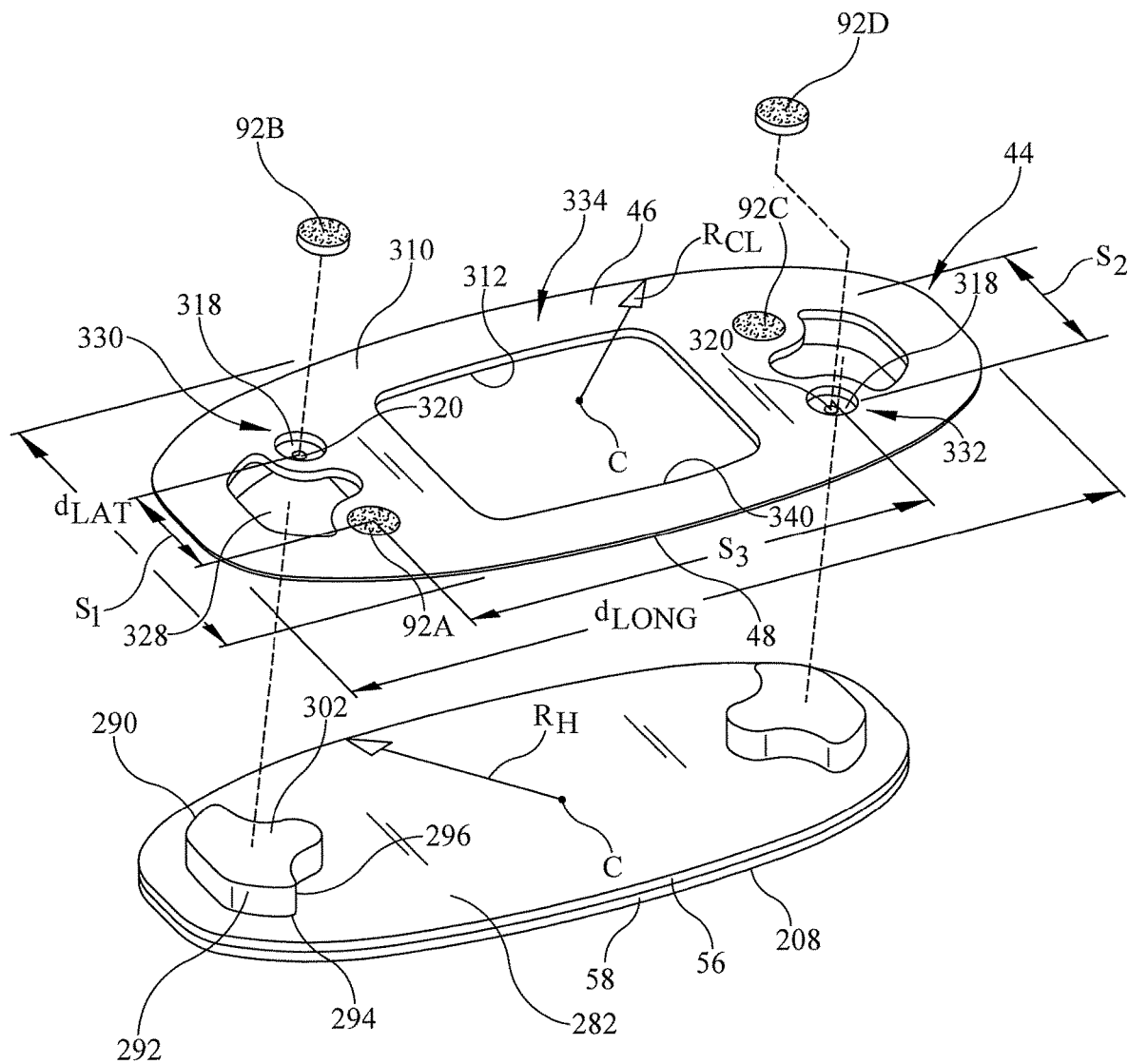
FIG. 30 is a view similar to that of FIG. 29 but showing the monitor as viewed from the cleat side.
Figure 31:
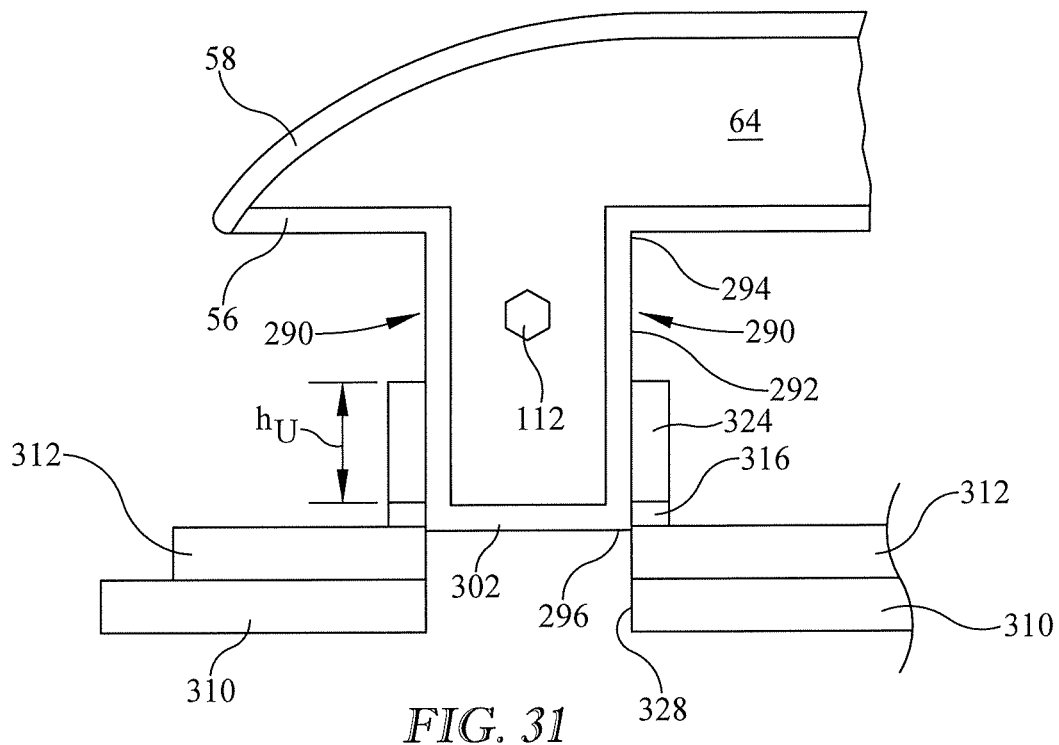
FIG. 31 is a view in the direction 31-31 of FIG. 29 showing the housing and cleat in close proximity to each other but not fully mated to each other.
Figure 32:
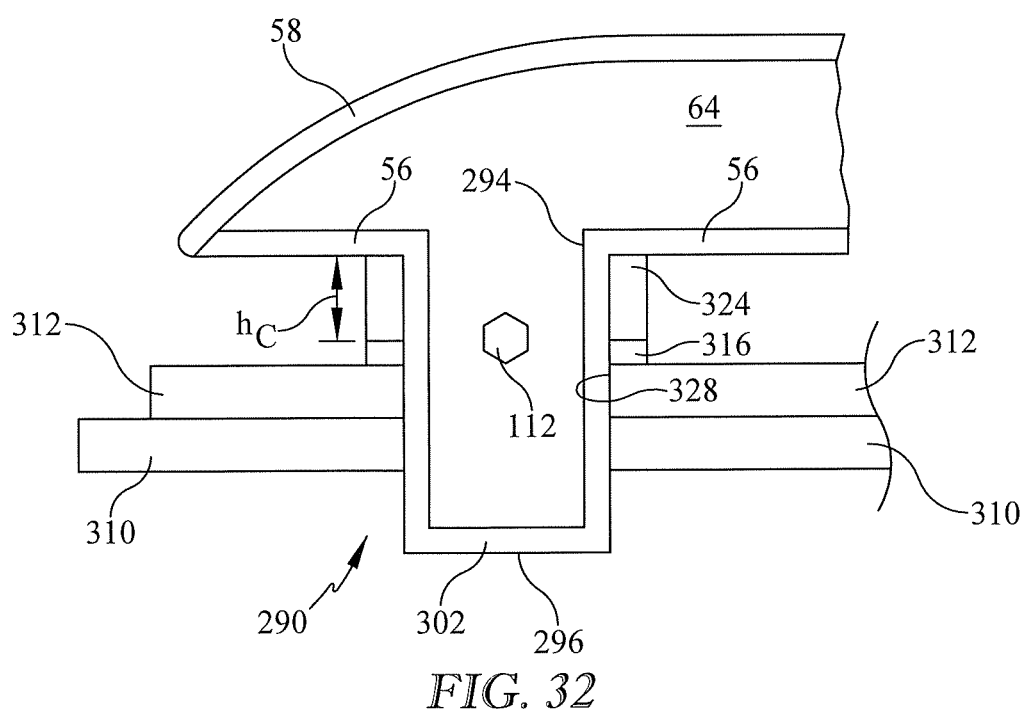
FIG. 32 is a view similar to FIG. 31 showing the cleat and housing fully mated to each other.
Figure 33:
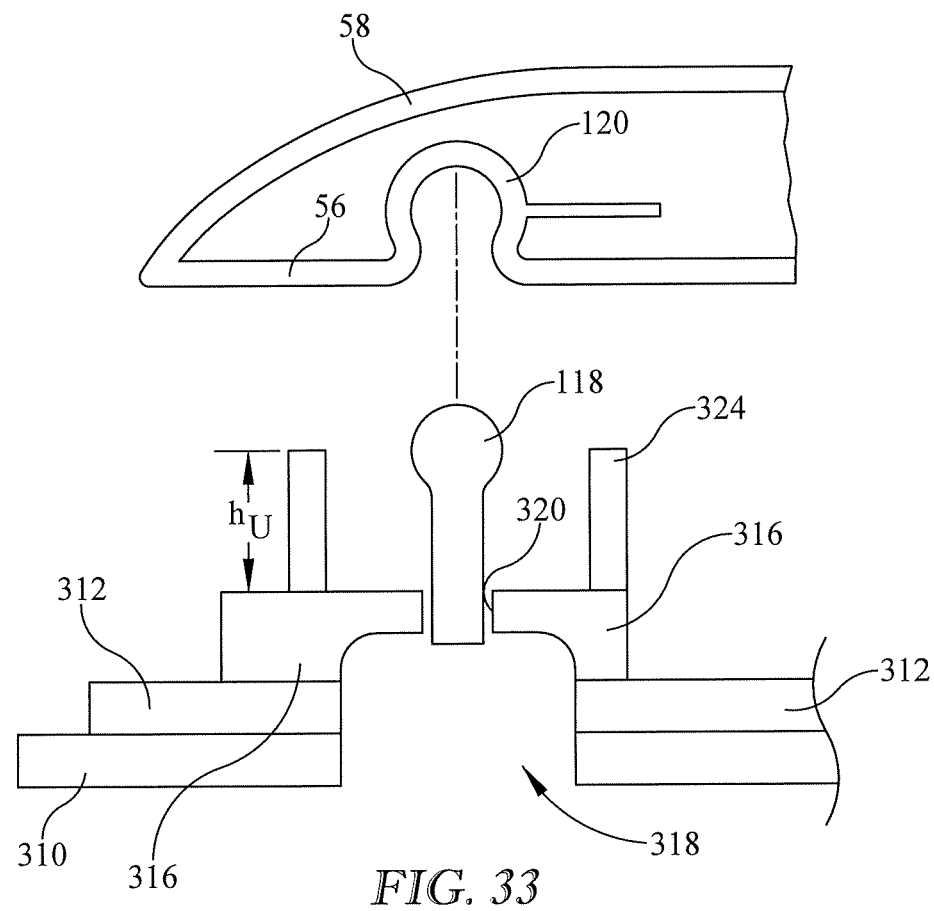
FIG. 33 is a view in the direction 33-33 of FIG. 29.
Figure 34:
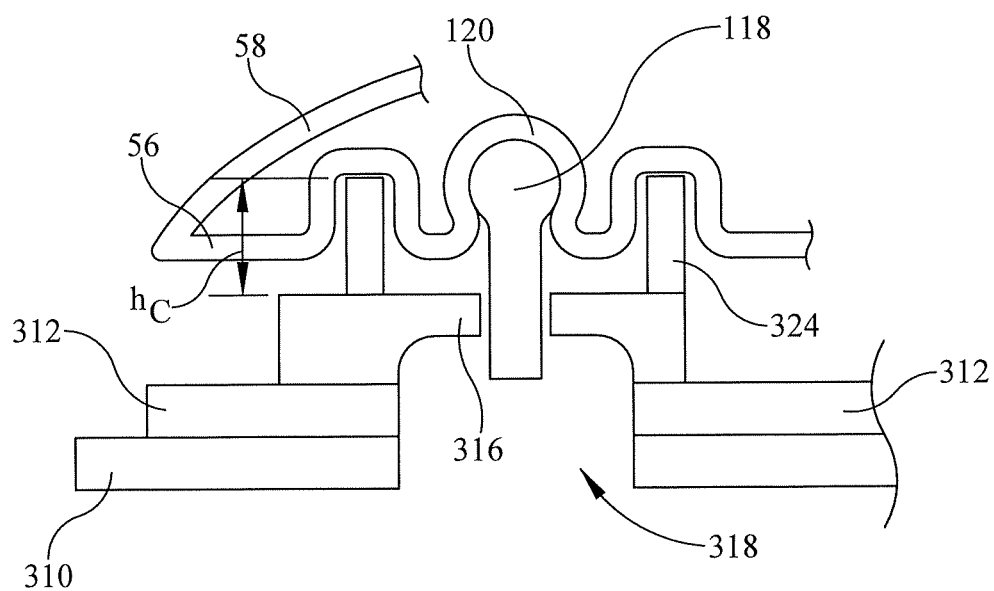
FIG. 34 is a view similar to FIG. 33 showing the cleat and housing fully mated to each other.

Cleat 44 also includes first and second electrode bases 316 secured to backing layer 312. The bases are the same as each other, therefore it will suffice to describe only one base. In one embodiment the electrode base is a rigid plastic member. As seen best in FIG. 33, at least one electrode pocket 318 extends part way through the electrode base. A smaller diameter aperture 320 extends the rest of the way through the electrode base. Referring to FIG. 30, an electrode 92, (individually identified as 92A, 92B, 92C, 92D) occupies each of the pockets and is exposed on the patient side of the cleat. In the illustrated embodiment the electrodes are hydrogel EKG electrodes.

Collectively, electrodes 92 form an electrode array comprising a first electrode pair (92A, 92B) and a second electrode pair (92C, 92D). The members of the first pair are spaced from each other by a first intrapair distance $S_1$. The members of the second pair are spaced from each other by a second intrapair distance $S_2$. The first and second intrapair distances are equal as illustrated, but may be unequal. The first electrode pair is spaced from the second electrode pair by an interpair distance $S_3$ which exceeds the intrapair distances $S_1$, $S_2$.

Cleat 44 also includes first and second gaskets or rings 324, each secured to one of the electrode bases. The rings are the same as each other, therefore it will suffice to describe only one ring. Each ring 324 may be a closed cell foam. When equipment housing 54 is attached to cleat 44, housing base 56 contacts and compresses the ring from an uncompressed height $h_U$ (FIGS. 31, 33) to a compressed height $h_C$ (FIGS. 32, 34) to provide a local liquid tight seal between the cleat and the housing. The compressed height may vary around the circumference of the ring.

A sensor opening 328 penetrates transversely through the cleat from the patient facing side 46 to the environment facing side 48. When housing 54 is attached to the cleat the sensor receptacle 290 of the housing registers with the sensor opening 328 of the cleat. Ring 324 and electrode base 316 circumscribe the receptacle, and the electrode bases reside transversely between contact layer 310 and ring 324. The receptacle wall portion 292 may extend transversely far enough that its cover 302 (or outer end 296 if no cover is provided) will be essentially flush with the patient's skin when the monitor is adhered to a patient. Alternatively the receptacle may be transversely short enough to not contact the patient's skin. In another alternative seen in FIG. 32, the receptacle projects transversely far enough to form a seal with the patient's skin which is tight enough to satisfy the requirements of sensor 112. Such a transversely elongated receptacle may have a bellows portion 196 as previously described in connection with FIG. 12.

Cleat 44 includes a cleat connector element 118. Housing 54 includes a housing connector element 120 which is connectable to and disconnectable from the cleat connector element thereby rendering the housing attachable to and detachable from the cleat. The illustrated cleat and housing connector elements 118, 120 are in the form of studs 118 and receptacles 120 as shown in FIGS. 9-13 but may take other forms. The studs and receptacles effect a mechanical connection between the cleat and the housing but may be adapted to also effect an electrical connection between the cleat and the housing.

The cleat has a longitudinal dimension $d_{LONG}$ and a lateral dimension $d_{LAT}$. The cleat includes a first measurement 330 site corresponding to the location of the first electrode pair 92A, 92B, and a second measurement site 332 longitudinally spaced from the first measurement site and corresponding to the location of the second electrode pair 92C, 92D. In the illustrated embodiment sensor receptacle 290 is locate at or near the measurement site, but could be located elsewhere. A transition portion 334 of the cleat extends between and joins the measurement sites.

Transition portion 334 is a reduced adherence region by virtue of having a feature that makes the region less adherent to the patient's skin than would be the case if that feature were not present. The reduced adherence of the reduced adherence region allows the patient's skin to stretch more than would be the case if transition portion 334 were a "full adhesive" region. As a result the reduced adherence region reduces the likelihood that the cleat will become dislodged from the patient's skin.

Figure 35:
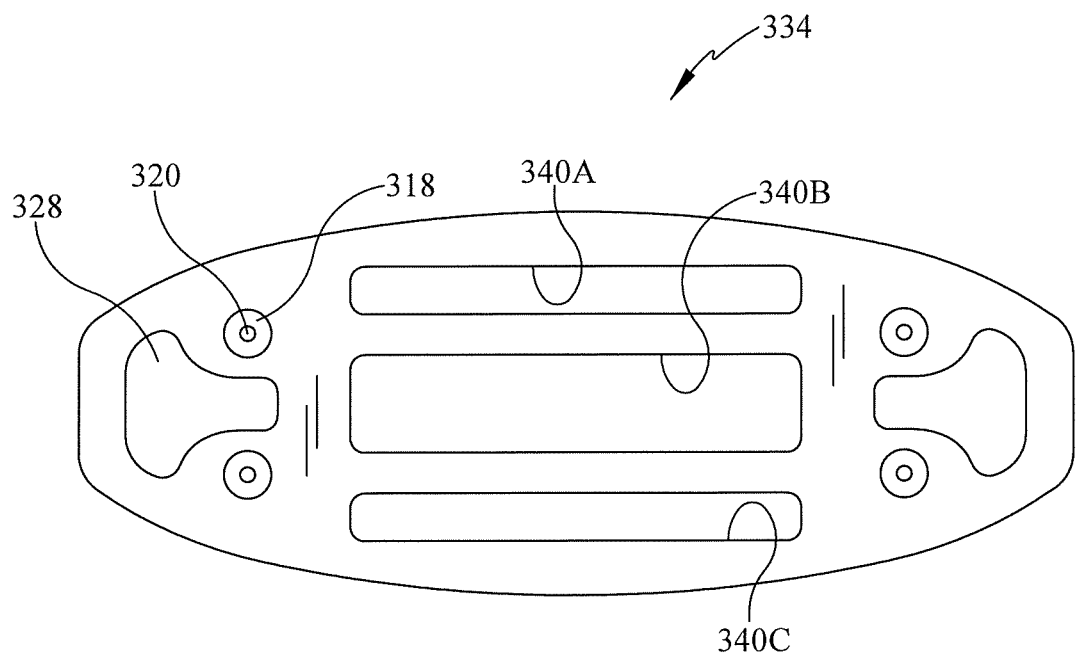
FIGS. 35-40 are plan views of the patient side of the single cleat embodiment of the vital signs monitor as seen from the cleat side thereof showing various configurations of a transition portion of the cleat.

In one embodiment the feature which results in the reduced adherence of transition portion 334 is a window 340 as seen in FIG. 30. If the window were not present, and if the adhesiveness of contact layer 310 were spatially uniform, transition portion 334 would not be a reduced adherence region. The presence of window 340 causes transition portion 334 to be a reduced adherence region. As seen in FIG. 35 the reduced adherence of the transition portion may be the result of two or more windows such as windows 340A, 340B, and 340C.

Figure 36:
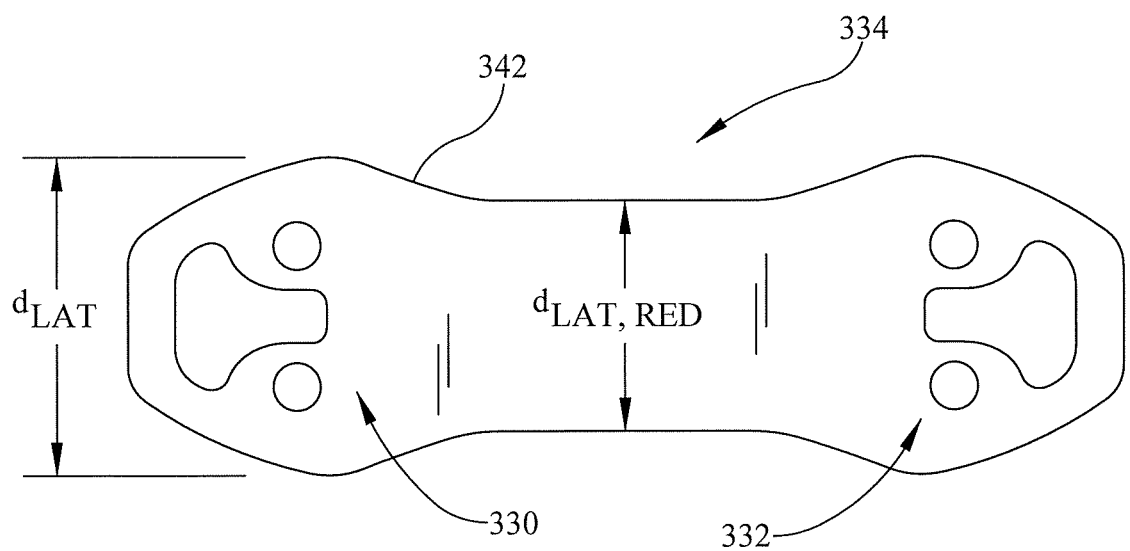

Referring to FIG. 36, in another embodiment the feature which results in the reduced adherence of transition portion 334 is a neck 342. The neck is defined by a dimension $d_{LAT,RED}$ which is smaller than the maximum lateral dimension $d_{LAT}$. If the neck were not present, and if the adhesiveness of contact layer 310 were spatially uniform, transition portion 334 would be laterally wider (e.g. as in FIG. 35) and therefore would not be a reduced adherence region. The presence of neck 342 causes transition portion 334 to be a reduced adherence region.

Figure 37:
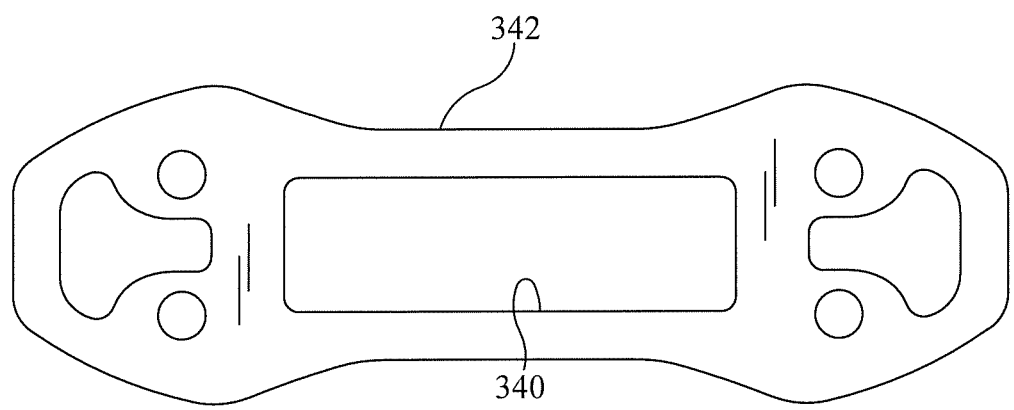

FIG. 37 shows an embodiment in which the feature which results in the reduced adherence of transition portion 334 is the combination of a neck 342 and a single window 340.

Figure 38:
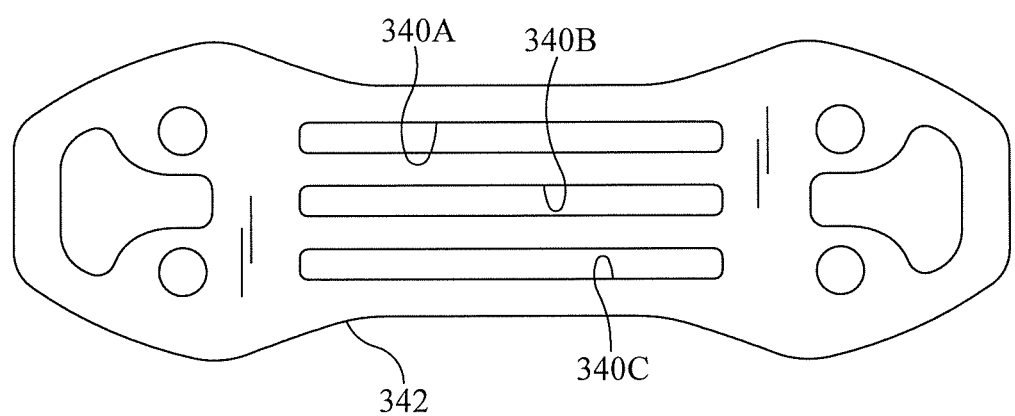

FIG. 38 shows an embodiment in which the feature which results in the reduced adherence of transition portion 334 is the combination of a neck 342 and multiple windows 340A, 340B, 340C.

Figure 39:
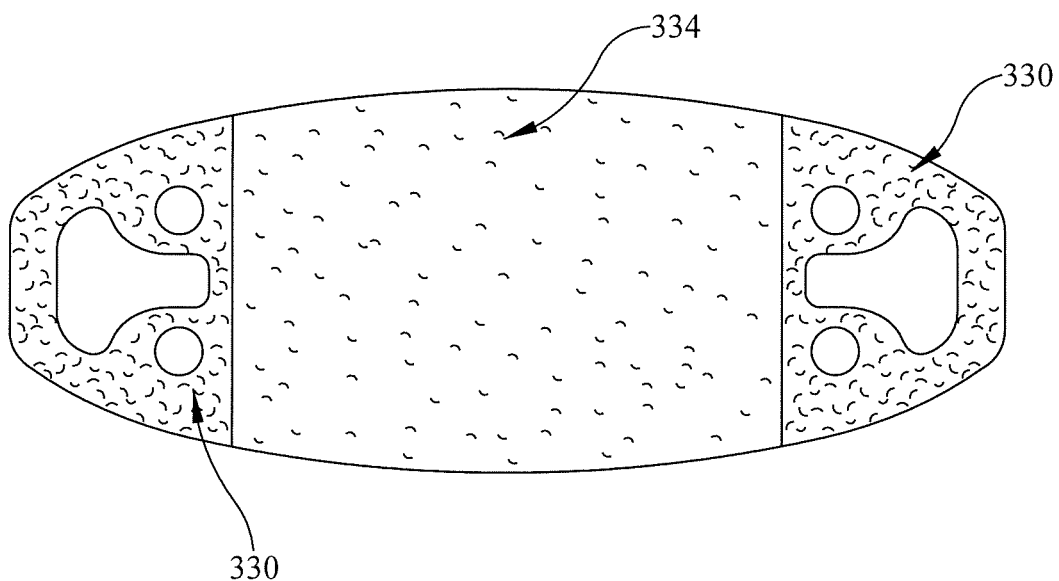
Figure 40:
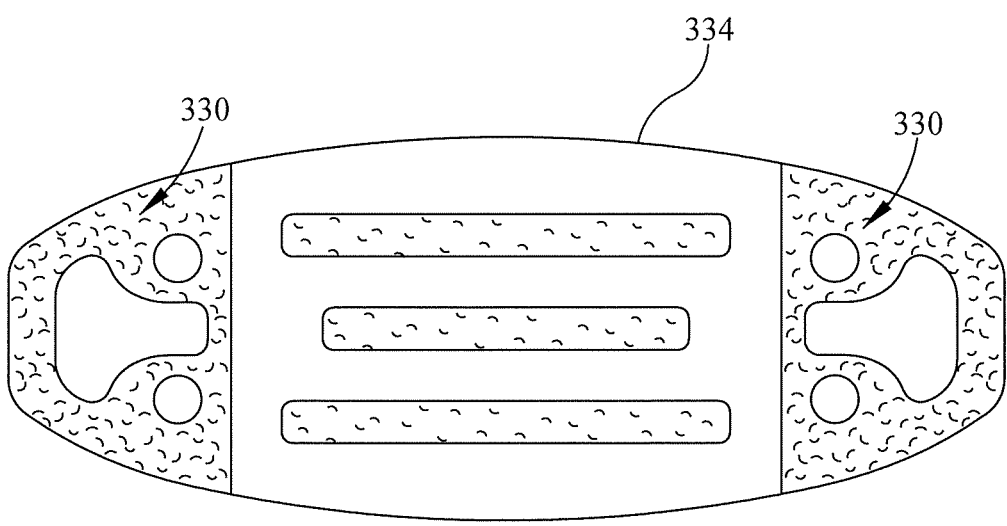

Referring to FIG. 39, in another embodiment the feature which results in the reduced adherence of transition portion 334 is under adhesiveness. As used herein. "under adhesiveness" refers to a condition in which a portion of contact layer 310 is less adhesive than another portion of layer 310. In FIG. 29 the longitudinal extremities of the cleat have a first adhesiveness indicated by relatively higher density stippling. Transition portion 334 has a second adhesiveness indicated by relatively lower density stippling. The second adhesiveness is less than the first adhesiveness and includes the limit case of no adhesiveness. FIG. 39 shows an abrupt change in adhesiveness. Alternatively the change could be graduated. FIG. 40 shows transition portion 334 as mostly nonadhesive (no stippling) but with adhesive strips which may or may not be as adhesive as the longitudinal extremities of the cleat.

The cleats for the various embodiments of the vital signs monitor described herein are for single patient use. Once a cleat is removed from a patient it is disposed of. The equipment module may be disposable or reusable.

We claim:

1. A vital signs monitor comprising:
   a subject wearable first cleat having a subject facing side, an environment facing side, a first sensor opening, and a pair of laterally spaced apart first electrodes;
   a subject wearable second cleat having a subject facing side, an environment facing side, and a pair of laterally spaced apart second electrodes;
   an equipment housing that is elongated and that has opposite end regions removably attached to the first and second cleats so as to overlap the first and second cleats to form an H-shaped arrangement when viewed from above, the equipment housing having a first sensor pocket which aligns with the first sensor opening; and
   a first sensor aligned with the first sensor opening and the first sensor pocket, wherein the first and second cleats are parallel with each other and each have portions that extend beyond opposite sides of the equipment housing in a symmetrical manner such that long dimensions of the first and second cleats are perpendicular with a long dimension of the equipment housing, wherein each electrode of the pair of laterally spaced apart first electrodes and each electrode of the pair of laterally spaced apart second electrodes includes a discrete element that contacts the subject to conduct electrical signals and that is coupled to a respective one of the portions of the first and second cleats that extend beyond the opposite sides of the equipment housing such that each discrete element, in its entirety, is positioned out from under the equipment housing.

2. The monitor of claim 1 wherein the first electrodes are on laterally opposite sides of the first sensor opening and the second electrodes are on laterally opposite sides of a longitudinally extending cleat reference line.

3. The monitor of claim 2 wherein the longitudinally extending cleat reference line is a centerline.

4. The monitor of claim 1 wherein the cleats are longitudinally spaced from each other, and wherein the longitudinal spacing of the cleats, the lateral spacing of the first electrodes from each other, and the lateral spacing of the second electrodes from each other causes a spatial distribution of the electrodes consistent with acquiring clinically useful electrocardiography signals.

5. The monitor of claim 1 wherein:
the first cleat includes a pair of first cleat connector elements, the first cleat connector elements being laterally offset from the sensor opening of the cleat in laterally opposite directions;
the second cleat includes a pair of second cleat connector elements, the second cleat connector elements being laterally offset from a longitudinally extending reference line of the second cleat in laterally opposite directions;
the equipment housing includes housing connector elements; and
the equipment housing is removably attached to the first and second cleats by way of a mating relationship between the cleat connector elements and the housing connector elements.

6. The monitor of claim 5 wherein the cleat and housing connector elements define one or more mechanical connections between the cleats and the housing, and wherein at least one of the mechanical connections also defines an electrical connection between the cleats and the housing.

7. The monitor of claim 1 wherein:
the first cleat includes exactly one first cleat connector element;
the second cleat includes exactly one second cleat connector element;
the equipment housing includes a first housing connector element and a second housing connector element; and
the equipment housing is removably attached to the first and second cleats by way of a mating relationship between the first and second cleat connector elements and first and second housing connector elements.

8. The monitor of claim 7 wherein each mating cleat and housing connector element pair circumscribes an electrical pathway which connects electrical elements associated with the housing to the electrodes or to electrical elements associated with the electrodes.

9. The monitor of claim 8 wherein the first sensor opening and the first sensor pocket define a sensor cavity, and the sensor resides in the sensor cavity.

10. The monitor of claim 7 wherein each mating cleat and housing connector element pair is configured so that the mating relationship between the housing and a given one of the cleats establishes both a cleat-to-housing mechanical connection and an electrical connection between the electrodes of the given cleat and electrical elements associated with the housing.

11. The monitor of claim 1 wherein:
the second cleat includes a second sensor opening and a second pair of ECG electrodes, and the equipment housing includes a second sensor pocket which aligns with the second sensor opening, the monitor also including a second sensor aligned with the second sensor opening and the second sensor pocket.

12. The monitor of claim 11 wherein the first sensor and the second sensor are the same type of sensor.

13. The monitor of claim 1 wherein at least one of the first and second cleats includes an adhesive and a protective liner covering the adhesive, the liner being folded or foldable to define a first liner portion in contact with the adhesive and a second liner portion separated from the adhesive by the first portion.

14. The monitor of claim 1 wherein at least one of the first and second cleats includes a registration notch which is adapted for use by a caregiver to mark a position of the cleat on the subject.

15. The monitor of claim 1 further including a standoff feature.

16. The monitor of claim 1 further including a satellite sensor.

17. A vital signs monitor comprising:
a subject wearable first cleat having a subject facing side, an environment facing side, a first sensor opening, and a pair of laterally spaced apart first electrodes;
a subject wearable second cleat having a subject facing side, an environment facing side, and a pair of laterally spaced apart second electrodes; and
an equipment housing that is elongated and that has opposite end regions removably attachable to the first and second cleats so as to overlap the first and second cleats to form an H-shaped arrangement when viewed from above, the housing having a first sensor pocket which aligns with the first sensor opening when the equipment housing is attached to the cleats, wherein the first and second cleats are parallel with each other and each have portions that extend beyond opposite sides of the equipment housing in a symmetrical manner such that long dimensions of the first and second cleats are perpendicular with a long dimension of the equipment housing, wherein each electrode of the pair of laterally spaced apart first electrodes and each electrode of the pair of laterally spaced apart second electrodes includes a discrete element that contacts the subject to conduct electrical signals and that is coupled to a respective one of the portions of the first and second cleats that extend beyond the opposite sides of the equipment housing such that each discrete element, in its entirety, is positioned out from under the equipment housing.

* * * * *